(12) United States Patent
Cherubini et al.

(10) Patent No.: US 10,436,685 B2
(45) Date of Patent: Oct. 8, 2019

(54) AUTOMATED SYSTEM FOR PROCESSING PARTICLES

(71) Applicant: Roche Diagnostics Operations, Inc., Indianapolis, IN (US)

(72) Inventors: Claudio Cherubini, Cham (CH); Martin Kopp, Huenenberg See (CG); Nenad Milicevic, Baar (CH); Daniel Mueller, Rotkreuz (CH); Emad Sarofim, Hagendorn (CH); Goran Savatic, Cham (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 226 days.

(21) Appl. No.: 15/417,858

(22) Filed: Jan. 27, 2017

(65) Prior Publication Data
US 2018/0010990 A1    Jan. 11, 2018

Related U.S. Application Data

(63) Continuation of application No. PCT/EP2015/067445, filed on Jul. 29, 2015.

(30) Foreign Application Priority Data

Jul. 30, 2014 (EP) ..................... 14179198

(51) Int. Cl.
*G01N 1/40* (2006.01)
*G01N 15/04* (2006.01)
(Continued)

(52) U.S. Cl.
CPC .......... *G01N 1/4077* (2013.01); *B01L 3/5021* (2013.01); *B04B 5/0407* (2013.01);
(Continued)

(58) Field of Classification Search
CPC ..... B01L 2300/0848; B01L 2300/0858; B01L 2300/168; B01L 2400/086; B01L 3/5021;
(Continued)

(56) References Cited

U.S. PATENT DOCUMENTS 1,019,022 A    3/1912 Cadwell
3,841,838 A   10/1974 Natelson
(Continued)

FOREIGN PATENT DOCUMENTS

CH    551221 A    7/1974
EP    0142105 A2    5/1985
(Continued)

*Primary Examiner* — Maureen Wallenhorst
(74) *Attorney, Agent, or Firm* — Roche Diagnostics Operations, Inc.

(57) ABSTRACT

A method for processing particles contained in a liquid biological sample is presented. The method uses a rotatable vessel for processing particles contained in a liquid biological sample. The rotatable vessel has a longitudinal axis about which the vessel is rotatable, an upper portion having a top opening for receiving the liquid comprising the particles, a lower portion for holding the liquid while the rotatable vessel is resting, the lower portion having a bottom, and an intermediate portion located between the upper portion and the lower portion, the intermediate portion having a lateral collection chamber for holding the liquid while the rotatable vessel is rotating. The method employs dedicated acceleration and deceleration profiles for sedimentation and re-suspension of the particles of interest.

6 Claims, 20 Drawing Sheets

(51) Int. Cl.
*G01N 35/00* (2006.01)
*G01N 35/10* (2006.01)
*B01L 3/00* (2006.01)
*B04B 11/04* (2006.01)
*B04B 13/00* (2006.01)
*B04B 5/04* (2006.01)
*B04B 7/08* (2006.01)
*C12M 1/00* (2006.01)

(52) U.S. Cl.
CPC ............... *B04B 7/08* (2013.01); *B04B 11/04* (2013.01); *B04B 13/00* (2013.01); *C12M 47/02* (2013.01); *G01N 1/405* (2013.01); *G01N 15/042* (2013.01); *G01N 35/00584* (2013.01); *G01N 35/10* (2013.01); *B01L 2300/0848* (2013.01); *B01L 2300/0858* (2013.01); *B01L 2300/168* (2013.01); *B01L 2400/086* (2013.01); *G01N 2001/4083* (2013.01); *G01N 2015/045* (2013.01); *Y10T 436/111666* (2015.01); *Y10T 436/25375* (2015.01)

(58) Field of Classification Search
CPC ....... B04B 11/04; B04B 13/00; B04B 5/0407; B04B 7/08; C12M 47/02; G01N 15/042; G01N 1/405; G01N 1/4077; G01N 2001/4083; G01N 2015/045; G01N 35/00584; G01N 35/10; Y10T 436/11; Y10T 436/111666; Y10T 436/25; Y10T 436/25375
USPC ........ 436/43, 45, 63, 174, 177; 422/64, 527, 422/533
See application file for complete search history.

(56) References Cited

U.S. PATENT DOCUMENTS

| | | | |
|---|---|---|---|
| 4,639,242 A | | 1/1987 | Babson |
| 5,840,253 A | | 11/1998 | Chase et al. |
| 6,150,182 A | * | 11/2000 | Cassaday ................ B03C 1/288 210/222 |
| 9,186,672 B2 | * | 11/2015 | Amasia .................. G01N 21/07 |
| 2005/0054506 A1 | | 3/2005 | Bradley |
| 2009/0000690 A1 | | 1/2009 | Oldham et al. |
| 2009/0291818 A1 | | 11/2009 | Soares et al. |

FOREIGN PATENT DOCUMENTS

| | | |
|---|---|---|
| EP | 0143105 A2 | 5/1985 |
| EP | 0898977 A2 | 3/1999 |
| WO | 2008/156906 A1 | 12/2008 |
| WO | 2009/143343 A1 | 11/2009 |
| WO | 2010/127278 A1 | 11/2010 |
| WO | 2014/015177 A1 | 1/2014 |

* cited by examiner

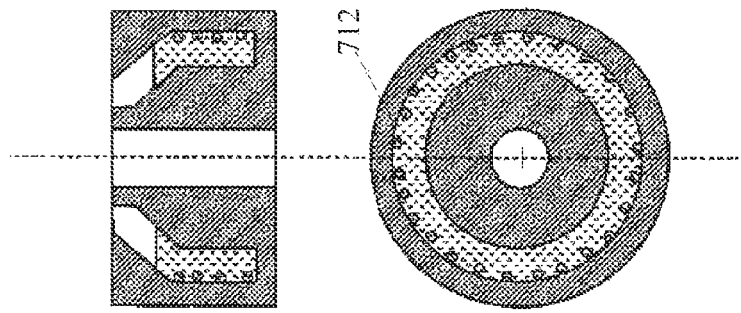
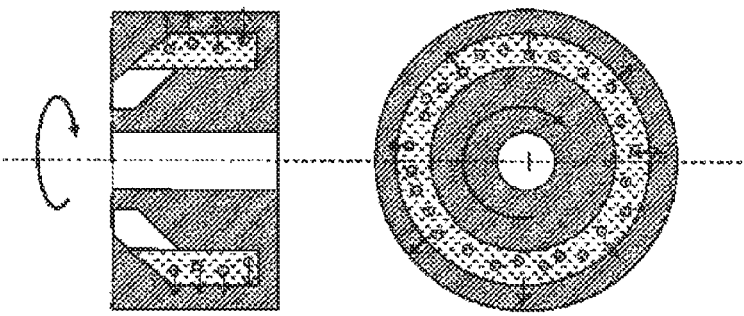
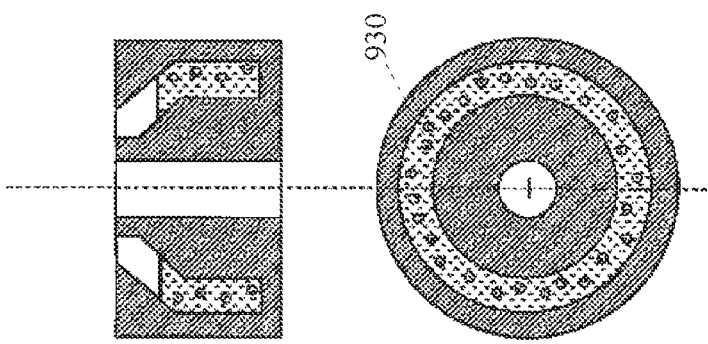
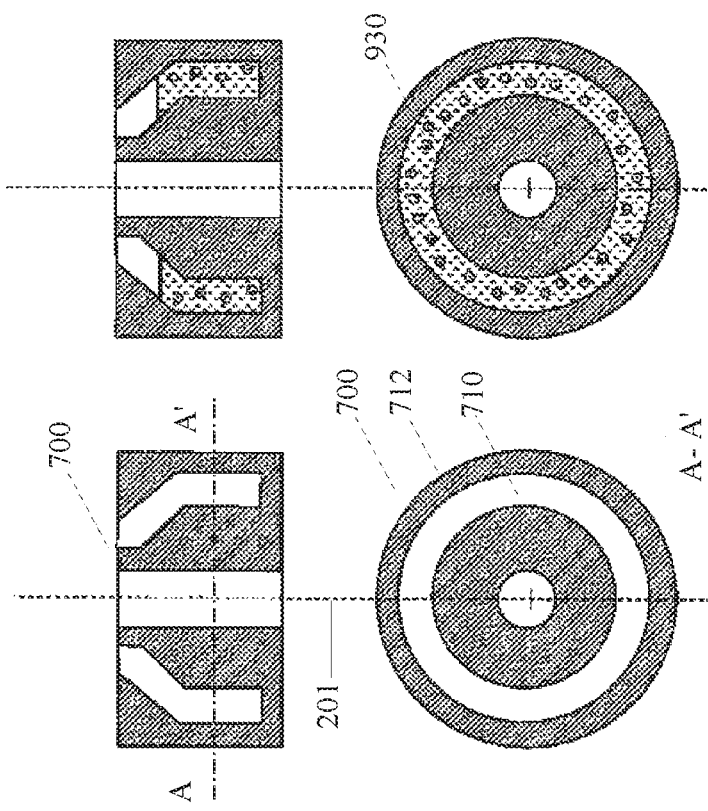

AUTOMATED SYSTEM FOR PROCESSING PARTICLES

CROSS-REFERENCE TO RELATED APPLICATIONS

This application is a continuation of PCT/EP2015/067445, filed Jul. 29, 2015, which is based on and claims priority to EP 14179198.8, filed Jul. 30, 2014, which is hereby incorporated by reference.

BACKGROUND

The present disclosure generally relates to processing particles in liquid biological samples for analytical purposes and, in particular, relates to an automated system for processing such particles with a rotatable vessel comprising a lateral collection chamber and to a method for processing particles in liquid biological samples.

Analytical applications for particles such as cells or artificial particles, especially in the field of clinical diagnostics, include flow cytometry, microscopy, cell counting, harvesting cells for or from cell cultures, and the like. Analytical methods for target molecules isolated with the help of binding particles are, for example, amplification and detection of nucleic acids such as RNA, DNA, mRNA (by means of PCR or other amplification techniques), ELISA or electro- or chemiluminescence assays for proteins, and the like.

A variety of different approaches have been taken to facilitate processing of such particles. For instance, classical centrifugation in which particles are typically sedimented at the bottom of tubes usually requires bulky centrifuges that take up a considerable amount of space in a clinical or other laboratory. Furthermore, retrieval of the supernatant after centrifugation may be hampered by the fact that a pipette or its tip should not touch and thus disturb the particle pellet at the bottom of the tube. Hence, the pipette or tip may not be inserted all the way to the bottom of the tube, resulting in a residual "dead" volume being a potential source for impurities or inhibitors of subsequent chemical reaction. This circumstance also impedes efficient automation of particle processing. Besides, usually batch processes are used, and the often large centrifuges imply relatively long distances for sedimentation, effectively slowing down the process. One variant of an automated device for processing particles is a test tube containing blood cells is mounted on a rotatable spindle, the latter including central passageways for the introduction of wash fluid and air into the test tube, and radial exit passageways at the bottom of the spindle. A vacuum is applied to the exit passageways so cell supernatant is aspirated out through them. This setup requires an intricate set of fluid and gas connections, and means for applying positive or negative pressure, thus complicating assembly as well as usability of such a system.

The likewise widely-used approach relying on filters for retaining particles is also not well amenable to automation, especially in view of the fact that the re-suspension of particles mostly requires manual steps.

In other systems in the field, the particles to be processed are bound to magnetic beads, or the particles themselves have magnetic properties. While this technology has been automated in the art, various problems have been encountered, such as clotting of magnetic beads resulting in dead volumes, or disturbance of downstream applications due to the presence of magnetic beads. Furthermore, respective automated system all require a magnet which takes up space and still needs to be brought into the close vicinity of a vessel or pipette holding the magnetic beads or particles, raising the need for complicated geometrical solutions and reducing flexibility when designing a respective automated system for processing particles.

Microfluidic devices, as an alternative technology used in the art, allow particle processing by exploiting the particles' hydrodynamic properties. Such devices usually contain microstructures of about 5 to 100 μm. It is, however, difficult to attain to a sufficient volume of such systems in order to permit medium to high throughput, as increasingly required in the clinical diagnostic environment, especially in terms of processed volume per time.

Generally, the automated processing of particles is relatively complex and requires a considerable number of distinct processing steps, with each step requiring its own instrument structure(s). Such steps include retaining particles in suspension, separation of particles, removal of supernatant from separated particles, re-suspension of particles, optical analysis of the particles, and the like.

Therefore, there is a need for an automated system that reduces the complexity of known automated system and also minimizes, or even abolishes, the need for manual intervention, thus contributing to cost efficiency, usability and increased throughput of the system.

SUMMARY

According to the present disclosure, a method for processing particles contained in a liquid biological sample is presented. The method can use a rotatable vessel for processing particles contained in a liquid biological sample. The rotatable vessel can have a longitudinal axis about which the vessel can be rotatable, an upper portion comprising a top opening for receiving the liquid comprising the particles, a lower portion for holding the liquid while the rotatable vessel is resting, the lower portion comprising a bottom, and an intermediate portion located between the upper portion and the lower portion, the intermediate portion comprising a lateral collection chamber for holding the liquid while the rotatable vessel is rotating. The method can employ dedicated acceleration and deceleration profiles for sedimentation and re-suspension of the particles of interest.

Accordingly, it is a feature of the embodiments of the present disclosure to provide for an automated system that reduces the complexity of known automated system and also minimizes, or even abolishes, the need for manual intervention, thus contributing to cost efficiency, usability and increased throughput of the system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 8A-D illustrates a schematic overview of a workflow using the rotatable vessel having a narrow peripheral chamber for imaging according to an embodiment of the present disclosure.

DETAILED DESCRIPTION

Figure 1A:
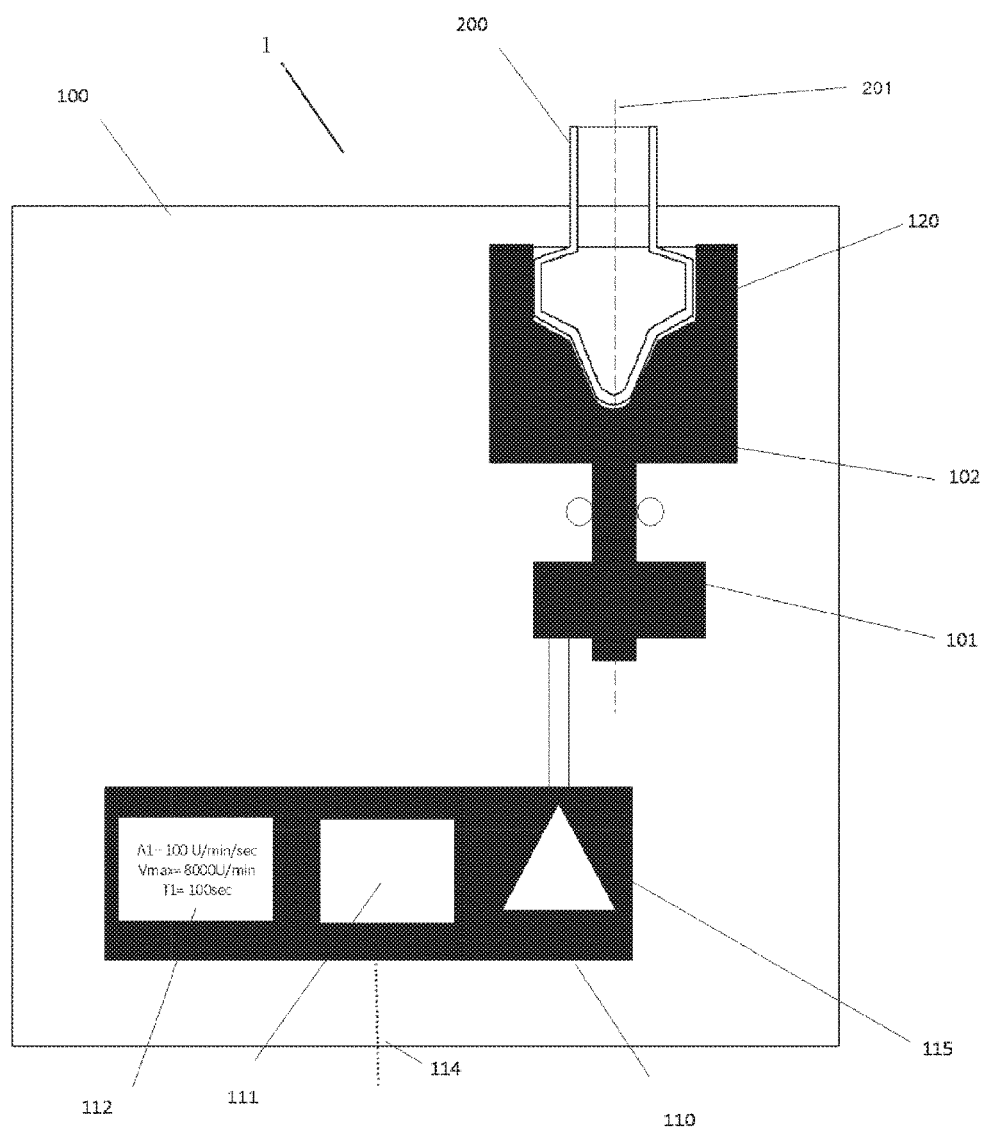
FIGS. 1A-C illustrate a schematic overview of the automated system described herein according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The shortcomings described above are addressed by the method, the rotatable vessel and the automated system described herein. The system can comprise a rotatable vessel for processing particles that may be contained in a liquid biological sample, whereby the particles can be of variable nature. For instance, the particles to be processed by the system may be living or dead cells from a human, such as blood cells, or unicellular pathogenic organisms or virus particles. The particles may also be of artificial nature and, for example, used to bind target analytes in the liquid biological sample. The rotatable vessel can be rotated about a longitudinal axis, and its structure can have at least an upper and a lower portion as well as an intermediate portion in between. The upper portion can have an opening, providing access for a pipettor or human operator. It can receive the liquid biological sample through its top opening, while the lower portion, having a bottom, can hold the liquid as long as the rotatable vessel is resting. When rotating the rotatable vessel, the liquid including the particles can move up towards a lateral collection chamber of the intermediate portion. Upon controlled stopping of the rotation, the liquid can settle down on the bottom of the lower part again, whereas the particles can remain in the lateral collection chamber of the intermediate portion and become thus at least partly separated from the liquid phase. The liquid may then be conveniently withdrawn from the bottom without disturbing or even retrieving the particles held within the lateral collection chamber.

The separated particles can then be re-suspended, washed, lysed, analyzed or elsewise further processed within or outside of the rotatable vessel. In order to accelerate, rotate and decelerate the rotatable vessel about its longitudinal axis, the automated system can also include a rotary actuator, and further a pipettor for handling the liquid biological sample with or without particles or other liquids that may be involved. Being an automated system, the system described herein can be controlled by a control unit.

In the context of automation, several advantages contribute to permitting the avoidance or at least reduction of manual steps. Notably, the pipettor can readily be introduced all the way to the bottom of the rotatable vessel, since the sedimented particles can reside in the lateral collection chamber. The automated system described herein can also allow for convenient re-suspension of the particles in the previous or other liquids that may be introduced into the rotatable vessel, by effecting a suitable rotational movement with defined profiles of acceleration and deceleration including optional directional changes, as described herein. The size and volume of the rotatable vessel can be highly flexible, and there may be multiple rotatable vessels present in the automated system, which may receive or contain different samples and may be actuated separately from each other. Such a setup can be apt to increase the system's overall throughput while processing a variety of samples or aliquots thereof at the same time. Moreover, "classical" centrifugal techniques such as differential centrifugation may be employed and even combination with other devices such as filters is possible, as described in the Examples.

An automated system for processing particles contained in a liquid biological sample is presented. The automated system can comprise a rotatable vessel for processing particles contained in a liquid biological sample. The rotatable vessel can comprise a longitudinal axis about which the vessel can be rotatable, an upper portion comprising a top opening for receiving the liquid comprising the particles, a lower portion for holding the liquid while the rotatable vessel is resting, the lower portion comprising a bottom, and an intermediate portion located between the upper portion and the lower portion, the intermediate portion comprising a lateral collection chamber for holding the liquid while the rotatable vessel is rotating. The automated system can also comprise a rotary actuator for rotating the rotatable vessel about its longitudinal axis in a controlled manner, a pipettor for introducing the liquid biological sample into the rotatable vessel and/or retrieving it therefrom, and a control unit for controlling the automated system.

The automated system described herein can address a number of problems in the art. As discussed above, the system can allow for efficient automated processing of particles contained in a liquid biological sample. A number of components required by other technologies in the art may be omitted. For instance, no centrifuge carousels are needed, no vacuum application involving complicated fluid and gas connections, no magnets or magnetic beads and no microfluidic capillary systems. The automated system can further allow re-suspension, washing, staining or other processing methods within the same vessel. These features taken together can reduce the complexity of the automated system described herein and can also minimize or even abolish the need for manual intervention, thus contributing to cost efficiency, usability and increased throughput of the system.

At the same time, the automated system described herein may be readily combined with other technologies of the art, such as filter devices or magnets, enhancing the flexibility of the automated system for potential specific applications as described herein.

Terms

As used herein, the term "liquid biological sample" can refer to a liquid material that may potentially contain an analyte of interest. The sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The test sample can be pretreated prior to use, such as preparing plasma from blood, diluting viscous fluids or diluting in general, lysis or the like. Methods of treatment can involve filtration, distillation, concentration, inactivation of interfering components, and the addition of reagents. A biological sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the biological sample can be suspected to contain a certain antigen or nucleic acid.

The "particles" contained in the liquid biological sample can be living or dead organisms or non-living material. In some embodiments, the particles can be pathogens such as bacteria or viruses, or bacteriophages. Among such pathogens, there may be viruses like HIV, HBV, HCV, CMV, WNV, SLEV, JEV, HSV, influenza, or other viruses. Other pathogens of interest may be bacteria, such as the genera *Neisseria, Chlamydia, Mycobacterium, Yersinia, Borrelia, Proteus, Enterococcus, Staphylococcus* such as methicillin-resistant or -sensitive *Staphylococcus aureus, Meningococcus, Escherichia, Clostridium*, or other bacteria. Also, fungi may be pathogenic particles of interest, for example, the genera *Candida, Aspergillus, Saccharomyces*, or other fungi. Also in some embodiments, the particles can be living or dead eukaryotic cells. In some of these embodiments, the particles can be human cells, such as blood cells, including white blood cells (WBC) such as monocytes, granulocytes (basophilic, eosinophilic, or neutrophilic ones), macrophages, T-lymphocytes or B-lymphocytes, plasma cells, or lymphatic or myeloic stem cells, thrombocytes, erythrocytes, circulating tumor cells, a mixture of different blood cells and/or tumor cells, or other healthy and/or malignant blood cells. In other embodiments, the particles can be cells derived from a tissue or from tissue culture or bacterial cultures. In further embodiments, the particles may be subcellular structures such as organelles, including mitochondria, nuclei, lysosomes, proteasomes, chaperonines, and the like.

In embodiments where the particles are non-living material, they may be particulate material such beads, grains, fleece, powder, or ground solid matter. In some embodiments, they can be analyte binding particles for binding specific biological targets which may, for example, be molecules, cells or viruses. In those embodiments, the particles may have surfaces coated with specific or unspecific binding molecules, such as nucleic acid capture probes, oligo- or poly(dT)-strands for binding mRNA, protein A for binding the Fc parts of immunoglobulins, Fab fragments of antibodies for binding specific proteins, nickel for binding histidine tags, streptavidin or biotin, integrins, adhesins, or other cell-surface molecules, or the like. In some embodiments, the biological target molecules can be cell surface molecules, such that specific cells may be captured by the analyte binding particles. For example, for blood samples, suitable antibodies specifically binding to cell surface antigens of leucocytes, erythrocytes, monocytes are known to people skilled in the art, for example, CD2/CD3 for T cells, CD14 for monocytes, CD15 for granulocytes and monocytes, CD16 for macrophages, CD36 for platelets, monocytes and macrophages, CD45 for leucocytes. In further embodiments, the analyte binding particles can have a metal-oxide or silica surface. Silicon dioxide surfaces such as glass surfaces may be used to bind nucleic acids in the presence of chaotropic agents.

"Chaotropic agents" can be substances that generally disturb the ordered structure of water molecules in solution and non-covalent binding forces in and between molecules. They can make several contributions to the procedure of sample preparation. Besides, chaotropic agents can contribute to the disruption of biological membranes, such as plasma membranes or the membranes of cell organelles if present. Non-limiting examples of chaotropic agents are guanidinium salts like guanidinium thiocyanate, guanidinium hydrochloride, guanidinium chloride or guanidinium isothiocyanate, urea, perchlorates such as potassium perchlorate, other thiocyanates or potassium iodide or sodium iodide.

The term "lateral collection chamber" can denote a cavity of the intermediate portion of the rotatable vessel described herein. "Lateral" can mean that the collection chamber can extend in a substantially horizontal direction and thus at an angle, in some embodiments substantially perpendicular, to the longitudinal axis about which the vessel is rotatable. The lateral collection chamber can be adapted and arranged to hold the particles contained in the fluid biological sample either alone or with the liquid surrounding it. Exemplary embodiments of the lateral collection chamber are described herein.

A "pipettor" can be a device allowing for the automatic withdrawing and/or dispensing of volumes of fluids such as for fluid transfer or sip and spit mixing. In the context described herein, these fluids can include the liquid biological sample, reagents used for processing the liquid biological sample, cleaning solutions, dilution buffers, processed liquids, liquids containing a processed analyte, or the like. The liquids may be withdrawn and dispensed from any of the following positions/vessels: sample tubes, intermediate process tubes, reagent containers, waste containers or positions, tip-wash-stations, output vessels, reaction tubes, and the like. In particular, the pipettor may be used for the dispensing of a fluid biological sample into the rotatable vessel described herein, or withdrawing it therefrom. The pipettor can be in some embodiments driven by a pneumatic or hydraulic system. As a hydraulic liquid the pipettor may in some embodiments use water or a commonly used reagent.

The pipettor may comprise one or more reusable washable needles such as a steel needle, or use disposable pipette tips. The pipettor may be mounted to a transfer head that can be moved in one or two directions of travel in a plane, for example, with guiding rails and a third direction of travel orthogonal to the plane, with a spindle drive or the like. For instance, the pipettor may be moved horizontally between a primary sample tube and the rotatable vessel or another target position, and vertically in order to withdraw or dispense the liquid biological sample or other liquids. The pipettor may be integrated, i.e. built in a work-cell or be a module of the system operatively connected to a work-cell. The position and operation (including parameters such as volume, flow rate, direction of flow, or the like) of the pipettor can be controlled by a control unit, as described herein.

A "control unit" can control the automated system in a way that the necessary steps for the processing protocols can be conducted by the automated system. That can mean the control unit may, for example, instruct the automated system to conduct certain pipetting steps with a pipettor to mix the liquid biological sample with reagents, or the control unit can control the automated system to incubate the biological sample or reagents or mixtures of both for a certain time at a certain temperature, or the control unit controls the acceleration, speed of rotation, time of rotation and deceleration of the rotatable vessel described herein, or other related parameters. The control unit may receive information from a data management unit (DMU) regarding which steps need to be performed with a certain sample. In some embodiments, the control unit may be integral with the data management unit or may be embodied by a common hardware. The control unit may, for instance, be embodied as a programmable logic controller running a computer-readable program provided with instructions to perform operations in accordance with a process operation plan. The control unit may be set up to control, for example, any one or more of the following operations: loading, wasting or washing of the rotatable vessel described herein or pipette tips, moving or opening of sample tubes and reagent cassettes, pipetting of samples or reagents, mixing of samples or reagents, washing pipetting needles or tips, controlling of a detection unit such as light source, for example, by selection of the wavelength, or the like. In particular, the control unit may include a scheduler, for executing a sequence of steps within a pre-defined cycle time. The control unit may further determine the order of samples to be processed according to the assay type, urgency, and the like. The control unit may also receive data from a detection unit related to a measurement of parameter of the sample.

In some embodiments, the automated system described herein further can comprise a data management unit. A "data management unit" can be a computing unit for storing and managing data. This may involve data relating to the liquid biological sample to be processed by the automated system, or data relating to the steps to be carried out within the rotatable vessel. The data management unit may be connected to an LIS (laboratory information system) and/or an HIS (hospital information system). The data management unit (DMU) can be a unit within or co-located with the automated system. It may be part of the control unit. Alternatively, the DMU may be a unit remotely located from the analyzer. For instance, it may be embodied in a computer connected via a network to the automated system.

An "analytical work cell" can allow for the analysis of samples for diagnostic purposes. An analytical work cell may comprise units assisting with the automated handling, pipetting, dosing, and mixing of samples and/or reagents. The analytical work cell may comprise a reagent holding unit for holding reagents to perform the assays. Reagents may be arranged, for example, in the form of containers or cassettes containing individual reagents or groups of reagents, placed in appropriate receptacles or positions within a storage compartment or conveyor. It may comprise a consumable feeding unit. The analytical work cell may comprise a process unit and/or a detection unit whose workflow is optimized for certain types of analysis. Examples of such work cells are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

A "detection unit" can allow the detection, in a qualitative (yes or no), semi-quantitative and/or quantitative manner, of a parameter or a property of the liquid biological sample or a part thereof. Among others, such parameters or properties may include the presence or absence of a certain indicator related to an illness or a health status, a concentration of a substance, a concentration of a dedicated class of particles such as cells, viruses, beads or organelles, a concentration of an antibody, the presence or concentration of a nucleic acid sequence or other biological target molecule. In order to carry out detection, the detection unit may include, for example, secondary tubes or vessels to execute a reaction, reagents, containers, liquid handling structures such as pipettors, heating or cooling, mixers, detectors such as a photometer, a fluorometer, a luminescence meter, a microscope, a fluorescence microscope, a thermal cycler, a flow cytometer, a mass spectrometer, a nucleic acid sequencer, an optical scanner, or the like.

A "robotic manipulator" can be an automated manipulator configured to manipulate components of the automated system described herein. In some embodiments, it can be moved laterally (along an x- and/or y-axis) and vertically (along a z-axis). In some embodiments, the robotic manipulator can be moved within a part or all of the automated system. In order to be moveable, the robotic manipulator may be flexibly suspended and/or include a flexible robotic arm. For instance, movement may be facilitated by a rotatable robotic arm fixed to the bottom or the ceiling of the automated system described herein. Alternatively or additionally, movement may be achieved by a telescope arm. Also, the robotic manipulator may include a bipartite robotic arm rotatable at its base at the bottom of the automated system, wherein the two parts of the arm can be attached to each other via a hinge or another type of joint. By combined movement of the hinge and rotation of the arm at its base, the robotic manipulator may be moveable in all directions. It can, for example, include gripper arms that may serve for gripping and manipulating the rotatable vessel described herein, or other components of the automated system. In such embodiments, the robotic manipulator can be a gripper. Alternatively or additionally, the robotic manipulator can apply a vacuum or at least negative pressure. Such a structure can, for instance, be or include a vacuum cup.

The term "maximum radius", with respect to the rotatable vessel described herein, can refer to the maximum orthogonal distance from the longitudinal rotational axis (generally essentially vertical) of the rotatable vessel to one of its inner side wall surfaces. At a specific horizontal cross-section of the rotatable vessel, at a specific height, the radius may be different from one at a different height of the rotatable vessel. Likewise, within a certain portion of the rotatable vessel, such as the upper, intermediate, or lower portion, the radii may differ from each other, and may differ depending on at which height of the respective portion the radius is considered.

For instance, within the intermediate portion, the radius at a height of 5 cm, measured from the bottom of the rotatable vessel, may be smaller or larger than the radius of the radius measured at a height of 7 cm. In such embodiments, a portion may have a height where the radius can be as large as or larger than at any other heights of the respective portion. This radius can be termed the "maximum radius" of that particular portion.

Hence, the term "maximum radius of a portion" can mean the largest maximum radius found in a distinct portion. The same logic can apply to the maximum radius of the entire rotatable vessel.

In some embodiments of the automated system described herein, the upper portion can have a first maximum radius, the lower portion can have a second maximum radius, and the intermediate portion can have a third maximum radius larger than each of the first maximum radius and the second maximum radius.

In such embodiments, the larger maximum radius of the intermediate portion can be due to the presence of a lateral collection chamber extending farther than the walls of both the upper and the lower portion. Under the influence of centrifugal force, upon rotation of the rotatable vessel about its longitudinal axis, a liquid biological sample initially present in the lower portion of the rotatable vessel can move to the lateral collection chamber of the intermediate portion. As the maximum radius of the upper portion is smaller than the maximum radius of the intermediate portion, and because the volume of the lateral collection chamber is larger than the volume of the liquid biological sample, the sample can remain in the lateral collection chamber without leaving the vessel. Particles present in the biological sample with a density higher than the density of the suspending liquid can move towards the inner wall of the lateral collection chamber resulting in sedimentation. Upon controlled deceleration of the rotatable vessel, the liquid can flow back to the bottom of the rotatable vessel and thus to the lower portion, following gravity.

Using controlled acceleration/deceleration protocols, particles sedimented in the lateral collection chamber can be re-suspended in a liquid added to the rotatable vessel described herein.

The re-suspended particles can flow down to the lower portion of the rotatable vessel as soon as gravity supersedes any applied centrifugal force.

Embodiments

Automated System for Processing Particles Contained in a Liquid Biological Sample Referring initially to FIG. 1, FIG. 1A shows a scheme of an exemplary embodiment of the automated system (1) described herein. In the embodiment depicted in this figure, the automated system (1) can have a particle processing station (100) including a rotatable vessel (200). Within the particle processing station (100), the rotatable vessel (200) can be held by a rotor (102) via an adapter (120). The adapter (120) can act as a mechanical interface for establishing a force coupling between the rotor (102) and the rotatable vessel (200). The rotor (102) can be driven by a rotary actuator (101), as to allow a controlled circular motion of the rotatable vessel (200) held by the rotor (102). The rotatable vessel (200) can thereby be rotated about its rotational axis (201).

The automated system (1) of the embodiment shown here can further include a control unit (110) with several components. Following specific protocols, the automated system (1) may control the motion of the rotary actuator (101), including its speed, direction of rotation, acceleration, deceleration, the relative position of the rotatable vessel (200), or the like. In this embodiment, the control unit (110) can include a control program (111) carrying out the actions described above based on the data stored in a data management unit (112). In the depicted embodiment, the user may monitor or even manipulate the automated system (1) via a communication interface (114) of the control unit (110). The communication interface (114) may, for instance, include a display such as a touchscreen, or the like.

In order to supply the automated system (1), particularly the rotary actuator (101), with sufficient power, a power transducer (115) is also depicted in FIG. 1A as a part of the control unit (110).

Figure 1B:
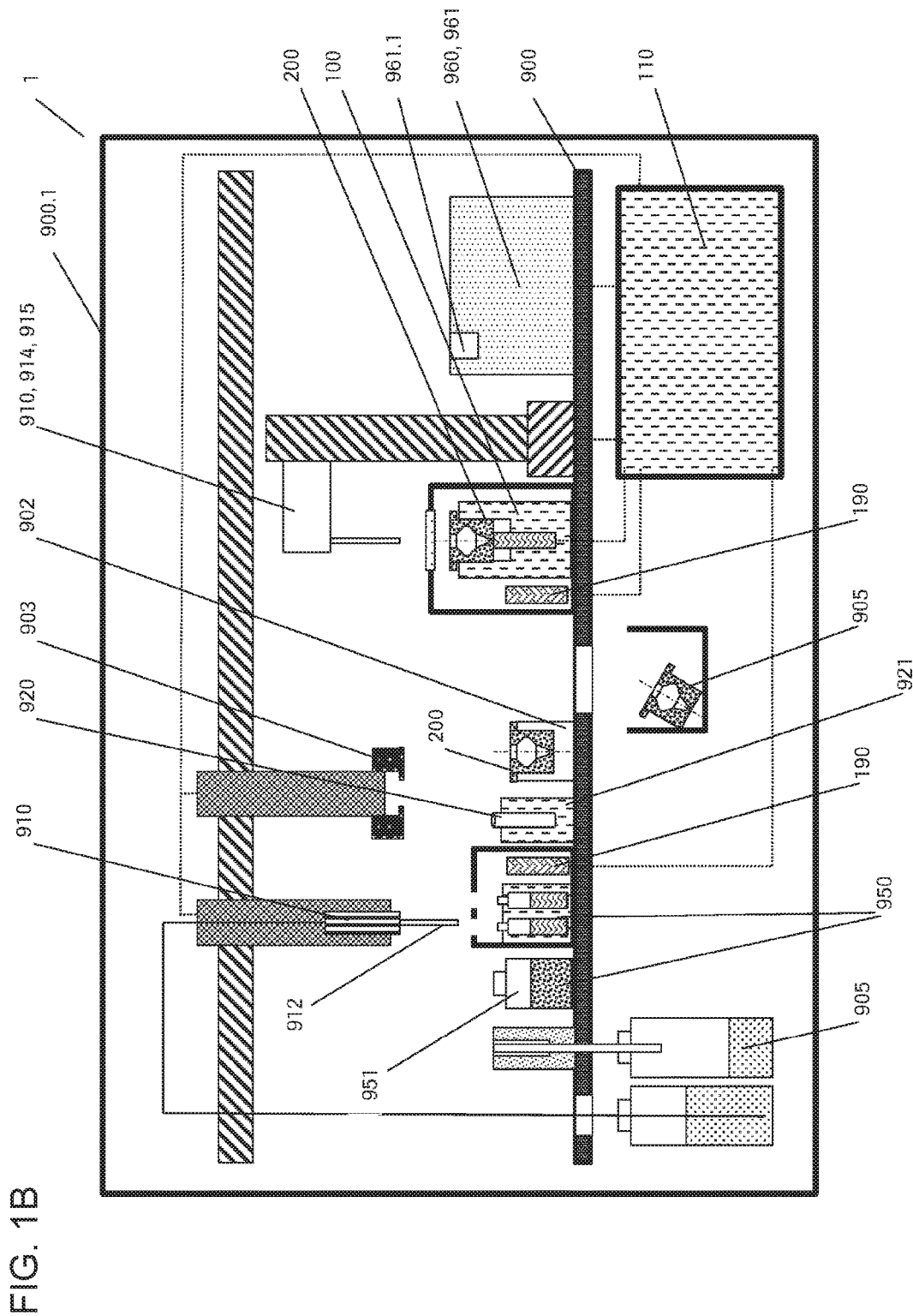

The automated system (1) described herein may further include other components for establishing convenient infrastructure, as shown in FIG. 1B. Among these other components there may be a baseplate (900) to which the particle processing station (100) can be attached. In some embodiments, more than one particle processing station (100) may be borne by the baseplate (900), thus increasing throughput and flexibility of the automated system (1).

Further, the automated system (1) may in some embodiments include a housing (900.1) shielding the process from the environment and vice versa.

The automated system (1) may also include a storage unit for unused rotatable vessels (200).

Also in some embodiments, the automated system (1) described herein can contain a rack (902) carrying a predefined number of rotatable vessels (200). The rack (902) may serve for loading and/or unloading one or a plurality of rotatable vessels (200) onto or from the particle processing station (100) or another component of the automated system (1).

In other embodiments, the automated system (1) may include a robotic manipulator (903) for transferring components within the automated system (1). As an example of a robotic manipulator (903), a gripper may be used for transporting a rotatable device (200) or other components and loading/unloading or locking/unlocking them at various positions within the automated system (1).

In some embodiments, the automated system (1) described herein can also include a waste container (905). Such a container (905) may be designated for liquid waste, or for solid waste, or both. The liquid waste container and/or the solid waste container may be comprised by a waste station.

Other components of the automated system (1) described herein may include, in some embodiments, one or more temperature control elements (190). A certain temperature may, for example, be required within the rotatable vessel (200) in order to carry out incubation for a chemical reaction to occur. Such reactions may include staining of cells or tissue, the binding of nucleic acids or antibodies, or the like. Different temperatures may be required in different steps of a processing method, such that the temperature control element or elements may include a thermostat for adapting and maintaining a specific temperature at a specific point in time. Suitable temperature control elements can include, for example, Peltier elements, air cooling or heating, or the like.

Furthermore, surveillance elements may be present in the automated system (1), such as systems for determining liquid levels (Liquid Level Detection=LLD), temperature sensors, sensors for detecting the presence of a sample (920) or a rotatable vessel (200), a rotary encoder for detecting speed, acceleration and position of the rotor (102), sensors and adaptive elements for controlling the air humidity within the automated system (1), and the like.

Hence, in some embodiments, the automated system (1) described herein further can comprise an air humidity control unit having a humidity sensor for measuring the air humidity within the automated system, and a nozzle for adjusting the air humidity.

The automated system (1) may further include fluid handling devices or systems in addition to the pipettor (910). The pipettor (910) or other components may be driven by a pump for driving any kind of liquid in and out of the rotatable vessel (200).

The automated system (1) may also include a wash station for cleaning the pipettor (910), for example, in case of a reusable steel needle, or pipette tips (912), if present. The pipettor (910) may be operated with the help of a system fluid transmitting pressure differences throughout the pipetting system including the pump. Such system fluids may, for instance, include water.

In the context of handling liquid biological samples (920), the automated system (1) may further include a sample supply unit (921) such as a feeder or another suitable structure for delivering samples to the automated system (1).

For identification of specific liquid biological samples (920), they may include an identification tag such as a one- or two-dimensional barcode, an RFID tag, or the like.

Further, the automated system (1) in some embodiments can include a sampler for withdrawing aliquots of a liquid biological sample (920) from a primary sample tube.

In some embodiments, a rotatable vessel (200) can be a disposable component, meaning that it can be used only once. In other embodiments, the rotatable vessel (200) may be reused for processing subsequent liquid biological samples (920) containing particles (930), or several repetitive steps, between which the rotatable vessel (200) can be cleaned in order to avoid carry-over contamination from one sample, analysis or step to another. In such embodiments, the rotatable vessel (200) may be mounted to the particle processing station (100). The cleaning steps may, for example, be effectuated by adding a wash buffer, or transferring the rotatable vessel (200) to a dedicated wash station. Wash reagents like the mentioned wash buffer may be delivered either by the pipettor (910), or by another dedicated transfer system (914) such as a syringe pump.

In some embodiments, such as the ones including washing the rotatable vessel (200), the cleaned rotatable vessel (200) may have to be dried after washing before being able to be reused. Residual wash buffer may, in some cases, be detrimental to further processing or analysis steps. Consequently, the automated system (1) may include a drying device (915). For instance, the drying device (915) may be a fan or similar device for blowing compressed air, in some embodiments heated air, into the rotatable vessel (200), or a heater for evaporating residual liquid from the rotatable vessel (200). FIG. 1B depicts an integrated unit including pipettor (910), wash buffer delivery system (914), and drying device (915).

The automated system (1) can further include, in some embodiments, reagents (950) or other liquids useful for the processing of particles (930) contained in a liquid biological sample (920). Such other liquids may include a wash buffer, a lysis buffer, a staining buffer, buffer for cell fixation, a buffer for cell perforation, a suspension of analyte binding particles, or the like. In such embodiments, the reagents (950) may be held in reagent containers (951) that may include identification tags such as barcodes or RFID tags.

Among these reagents (950), there may in some embodiments be a binding buffer for promoting adhesion of desired particles (930) to the inner wall of the lateral collection chamber (220) of the rotatable vessel (200).

Likewise, the reagents (950) may include an elution buffer suppressing the adhesion of the particles (930) to the inner wall of the lateral collection chamber (220) of the rotatable vessel (200).

In some embodiments, the automated system (1) described herein can include an analytic module (960) for analyzing the liquid biological sample (920) and/or the particles (930) contained therein. In this context, the term "analyzing" may mean to generate an analytical result either from the particles (930), such as in embodiments where the particles (930) are cells, or by the particles (930), in embodiments where the particles (930) are analyte binding particles or the like.

The analytical module (960) may include a particle analyzer (961) such as a flow cytometer, a cell counter like a Coulter counter, a digital microscope, a fluorescence-associated cell sorter (FACS) or cell counter, or the like. In such embodiments, the particle processing station (100) and the particle analyzer (961) may be part of an integrated system covering particle processing and analysis of the processed particles (930). Such an integrated system may include an automation interface (961.1). In such embodiments, the particle analyzer (961) may be adapted to receive the processed particles (930) directly from the rotatable vessel (200), without being transferred to an intermediate container. During analysis the rotatable vessel (200) may be rotated about its longitudinal axis (201) in order to avoid sedimentation of particles (930), since the latter may lead to false results.

Figure 1C:
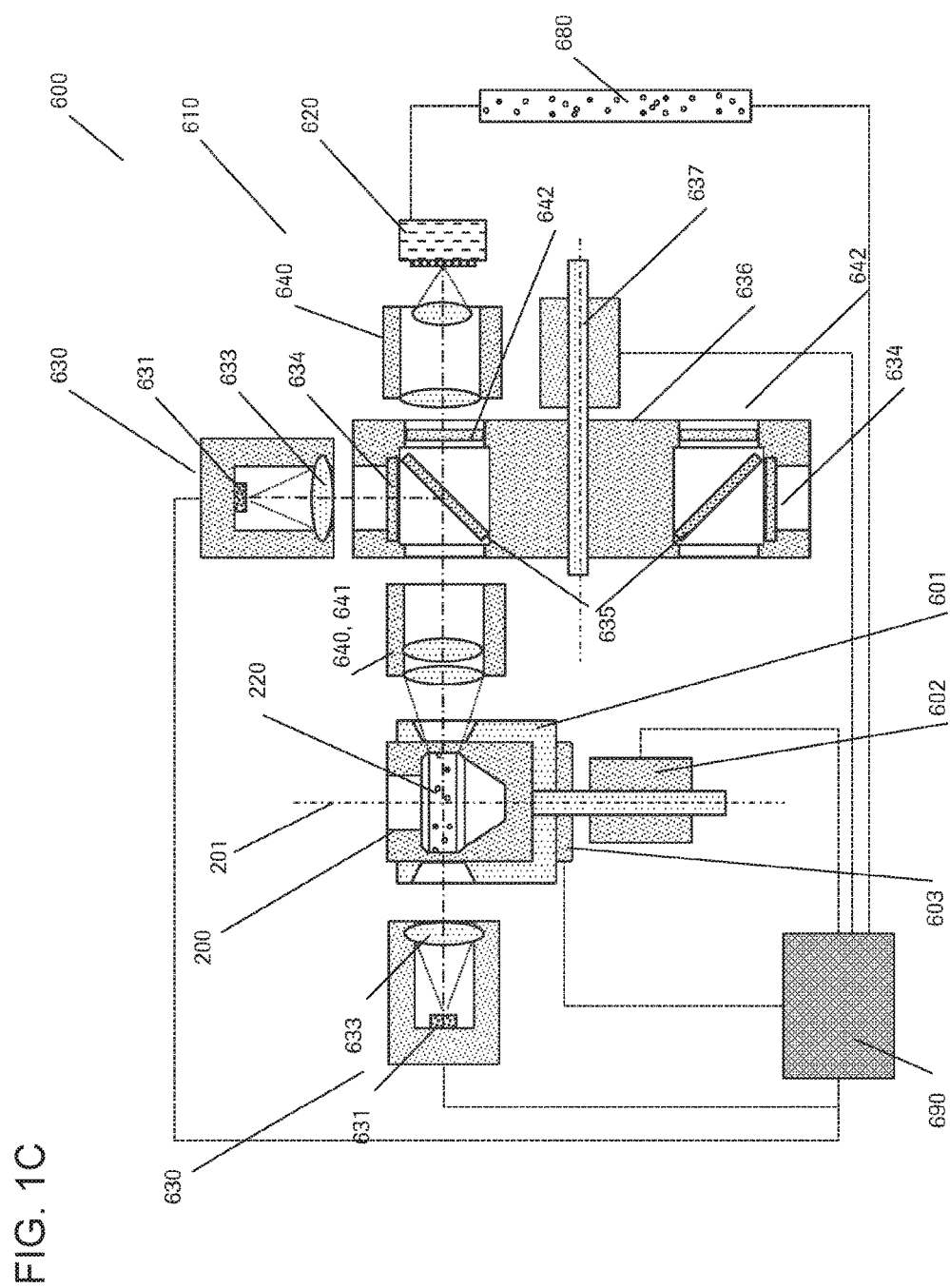

FIG. 1C shows a further component present in some embodiments of the automated system (1) described herein. It may be advantageous to include a scanner (600) in the automated system (1) in order to optically analyze the particles (930) within the rotatable vessel (200). Such optical analysis may include, for example, detecting the presence or absence of distinct particles (930), measuring their concentration or density on the surface, determining the ratio of multiple different particles (930), analyzing the status of certain particles (930), imaging the morphology of particles, classifying particles or the like.

The scanner (600) shown in this figure can have a precision holder (601) for accurately holding the rotatable vessel (200), a precision rotary drive (601) able rotate the rotatable vessel (200) precisely about its longitudinal axis (201), a precision encoder (603) allowing a precise and accurate positioning of the rotatable vessel (200) in a predefined position, and a detection unit (610) having a photonic detector array (620) including an illuminator (630) and imaging optics (640).

The photonic detectors array (620) can be a single line linear photodetector such as, for example, a linear photodiode array or a CMOS linear image array. It may also have several parallel detector arrays, each of them having its own filter(s), allowing for multispectral imaging. Also, the photonic detector array may carry its own (micro-) optics, able to increase sensitivity. The sensor may also be a so-called TDI-linear sensor array (TDI=time delay and integration). Together with the precision rotary drive (601), the photonic detector array can create an image (680) of the particles (930) present on the surface of the inner wall of the lateral collection chamber (220) of the rotatable vessel (200).

The illuminator (630) can provide a defined illumination of the lateral collection chamber (220) which is observed by the photonic detector array (620). The illuminator (630) may use front light (630*a*) or back light (630*b*).

The illuminator's (630) primary light source (631) may, for instance, be a halogen lamp, an LED, a white LED, a colored LED, a tungsten or mercury vapor lamp, a flash lamp, a laser, or the like. It may also be a multicolored LED, where the color of the LED can be tuned. The primary light source (631) may in some embodiments have an elongated shape to geometrically match its illumination target (220).

The illuminator (630) may have any optical elements (633) required to shape, to direct, to collimate or to homogenize the emitted light, such as lenses, diffusors, optical fibers, tapers, holographic elements, flat and hollow mirrors, or the like.

The illuminator (630) may have filters (634) in order to limit the base spectrum of the primary light source (631) to a defined range. Such filters (634) may include interference filters or absorption filters, tunable filters, or the like. The illuminator (630) may in further embodiments have dichroic mirrors or semitransparent windows (635). Also in some embodiments, the illuminator (630) may have mechanical means to switch filters (634), such as a dichroic-filter-wheel (636) and a corresponding drive (637).

As set out above, the scanner (600) may include imaging optics (640) adapted and arranged to direct the light as required, the imaging optics (640) in some embodiments including lenses or fibers, flat or hollow mirrors, an autofocusing device (641), a lens for compensating the bent imaging plane, such as a plan concave cylinder lens, or the like. In some embodiments, the imaging optics (640) can further include an optical filter (642) to limit the bandwidth of the observed light.

In the depicted embodiment, the scanner (600) can further include a control unit (690) for controlling elements of the scanner (600), including, for example, the position of the precision rotary drive (602), the status of the illuminator (630), selection of a distinct filter (642) in case several different filters are present, the focus of the autofocusing device (641), or the like. The control unit (690) may receive data regarding the monitored particles (930) from the photonic detector array (620) and may in some embodiments derive an analytical result from the data.

In some embodiments, the illuminator (630) may comprise a laser as a primary light source (631). Suitable detectors in such embodiments may be, for example, a single photonic sensor such as a photomultiplier, or the like. In such embodiments, the illuminator (630) may be moved along a mainly vertical direction (mostly parallel to the longitudinal axis (201) about which the rotatable vessel (200) is rotated) in order to receive photonic data, related to particles (930) present at the inner wall of the lateral collection chamber (220). Together with the precision rotary drive (601) the setup can generate a developed view of the surface and the particles (930) thereon. Together with a horizontal movement (in direction of the autofocus), even a three-dimensional image of the particles (930) may be obtained, contributing to overcome potential mechanical tolerances.

In further embodiments, the rotatable vessel (200) may include orientation marks on its inside, allowing for the identification of an absolute or relative position.

Also in some embodiments, no illuminator (630) may be required in case the detection is based on luminescence not depending on excitation by primary light.

The automated system (1) can include in some embodiments a rotatable vessel (700) with an annular peripheral chamber for imaging the particles (930) of interest.

Thus, another automated system (1) for optically analyzing particles (930) contained in a liquid biological sample (920) is presented. The automated system (1) can comprise a rotatable vessel (700) with an annular peripheral chamber (710) contained in a liquid biological sample (920). The rotatable vessel (700) can comprise a longitudinal axis (201) about which the vessel (700) is rotatable, a transparent outer wall (712), an upper portion (205) comprising a top opening (210) for receiving the liquid biological sample (920) comprising the particles (930), and an intermediate portion (206) located below the upper portion (205), the intermediate portion (206) comprising an annular peripheral chamber (710) for holding the liquid, the annular peripheral chamber (710) comprising on the surface of its inner wall a region of sedimentation (301) for the particles (930) contained in the liquid biological sample (920), wherein the annular peripheral chamber (710) is fluidically connected to the top opening (210). The automated system (1) can also comprise a rotary actuator (101) for rotating the rotatable vessel (700) about its longitudinal axis (201) in a controlled manner, a pipettor (910) for introducing the liquid biological sample (920) into the rotatable vessel (700) and/or retrieving it therefrom, a control unit (110) for controlling the automated system (1), and a scanner (600) comprising imaging optics (640) for optically analyzing the particles (930) contained in the liquid biological sample (920).

Rotatable Vessel

A rotatable vessel (200) for processing particles (930) contained in a liquid biological sample (920) is presents. The rotatable vessel can comprise a longitudinal axis (201) about which the vessel (200) is rotatable, an upper portion (205) comprising a top opening (210) for receiving the liquid biological sample (920) comprising the particles (930), a lower portion (207) for holding the liquid while the rotatable vessel (200) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (200) is rotating, the collection chamber (220) comprising on the surface of its inner wall a region of sedimentation (301) for the particles (930) contained in the liquid biological sample (920).

Figure 2A:
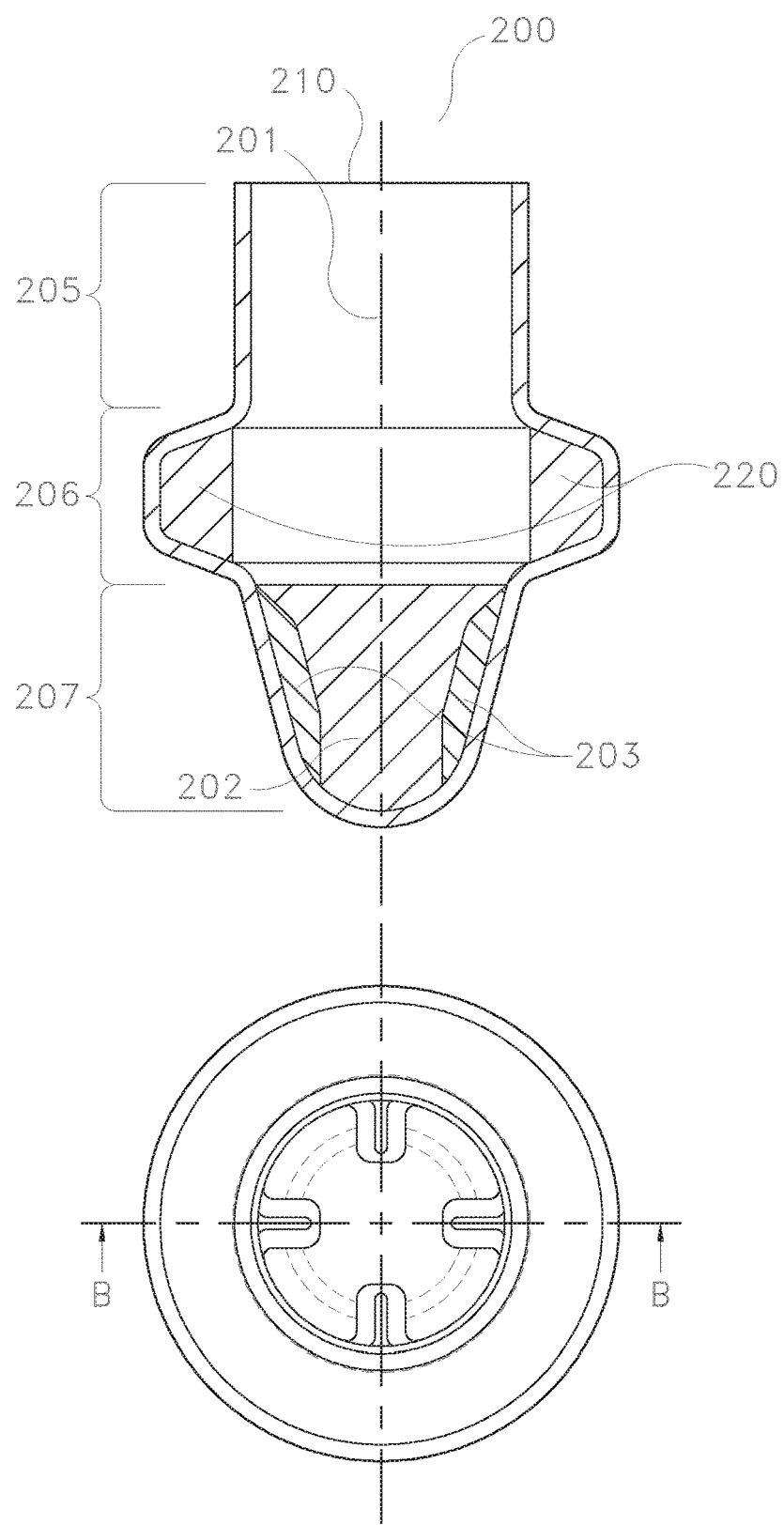
FIGS. 2A-F illustrate a schematic overview of the rotatable vessel described herein according to an embodiment of the present disclosure.

FIG. 2A depicts a scheme of an exemplary embodiment of the rotatable vessel (200) as a vertical cross-section (upper drawing) and as a top view (lower drawing). As set out above, such a rotatable vessel (200) may be suitable for a variety of methods, such as separation of particles from a liquid, or separation of different particles from each other based on different properties such as diameter and/or density, (re-)suspension or mixing of particles (930) in a liquid, cleaning/washing of particles, incubation for chemical reactions with or of the particles (930), and other applications. FIG. 2A shows the longitudinal axis (201) about which the vessel (200) is rotatable as a vertical broken line. In some embodiments, the axis (201) can be essentially parallel to the direction of gravity, in this case essentially vertical.

The figure also indicates the upper portion (205), the intermediate portion (206), and the lower portion (207) of the rotatable vessel (200).

As set out in the context of the automated system (1), in some embodiments of the rotatable vessel (200) described herein, the upper portion (205) can have a first maximum radius, the lower portion (207) can have a second maximum radius, and the intermediate portion (206) can have a third maximum radius larger than each of the first maximum radius and the second maximum radius.

The upper portion (205) can include a top opening (210) allowing the introduction or retrieval of liquid into or from the rotatable vessel (200). In some embodiments, the opening (210) may include a closure (211). In some of those embodiments, the closure (211) may be readily reopened and then closed again as the situation may require. Generally, the closure (211) can bring about the effect of protecting the liquid biological sample (920) from contamination and, on the other hand, protecting the environment from contamination by the sample (920), since especially clinical samples may contain pathogenic organisms or toxic substances. Further, the closure (211) can contribute to avoiding evaporation of any liquid inside the rotatable vessel (200) such as the liquid biological sample (920). Suitable closures (211) may be of different materials and may assume different shapes and colors. In some embodiments, the closure (211) can be a screw cap and can thus be screwed onto and unscrewed from the rotatable vessel (200). In other embodiments, the closure (211) can form a snap fit mechanism with the rotatable vessel (200). In some embodiments, the closure (211) can be a penetrable cap, such as a septum made of elastomer, of a silted foil, or of another penetrable material. In such embodiments, the inside of the rotatable vessel (200)

may be shielded from its surroundings before, after and during interaction with the pipettor (910), particularly in embodiments where the closure (211) is a penetrable septum of elastic material. In such embodiments, a pipetting needle may pierce the septum, dispense the liquid biological sample (920), be withdrawn again, and the resulting hole in the septum may substantially close again due to the elastic properties of the septum.

In this depiction, the lateral collection chamber (220) can form the intermediate portion (206) of the rotatable vessel (200) and extend around the perimeter of the vessel (200) in a circular manner. As described above, the lateral collection chamber (220) can be the place where the liquid biological sample (920) can mainly be located while the rotatable vessel (200) is rotating about its longitudinal axis (201). The current figure shows schematically how liquid within the lateral collection chamber (220) can be pressed to its inner walls by centrifugal force and can form, when exceeding a certain rotational acceleration, an essentially vertical surface. The lateral collection chamber (220) of this specific embodiment can have a volume of about 1.3 ml, as indicated in the figure. In other embodiments, the lateral collection chamber (220) may be split into several compartments which can be rotationally symmetric relative to the longitudinal axis (201).

The lower portion (207) is also shown schematically to contain liquid within its inner space (202). The liquid can form an even horizontal surface while the rotatable vessel (200) is resting. The walls of the lower portion (207) in this embodiment can be tapered and rounded, thus avoiding potential "dead corners" in which liquid may accumulate and be poorly accessible for the pipettor (910) Likewise, the intersections between the walls within a portion and/or the corners between portions (for example, between the lower (207) and the intermediate (206) portion or between the upper (205) and the intermediate (206) portion) can be, in some embodiments, rounded in order to avoid trapping liquid or particles (930) in a corner or forming liquid barriers.

Hence, in some embodiments of the rotatable vessel (200) described herein, the walls of the lower portion (207) can be tapered.

In further embodiments, the walls of the lower portion (207) can be rounded.

In yet further embodiments, the intersections between the walls within a portion and/or the corners between portions can be rounded.

Also, the lower portion (207) in the depicted embodiment can have a baffle (203). A baffle (203) can mediate the application of rotational acceleration from the inner walls of the rotatable vessel (200) to the liquid contained therein. In the present embodiment, it can protrude from the inner walls of the rotatable vessel (200) at its lower portion (207) and induce the liquid therein to rotate when the rotatable vessel (200) is rotated about its longitudinal axis (201).

Thus, in some embodiments of the rotatable vessel (200) described herein, the lower portion (207) can comprise a baffle (203).

The rotatable vessel (200) described herein may further include a thermal interface for being thermally controlled, or an identification tag such as a one- or two-dimensional barcode or an RFID tag, or the like. The rotatable vessel (200) may, in further embodiments, be optically shielded, for instance, in order to reduce the risk of degradation of photo-sensitive sample components, particles (930) or reagents. Such shielding may be conferred by measures such as opaque walls of the rotatable vessel (200). In such embodiments, the rotatable vessel (200) may include a window or other suitable optical interface in order to observe or otherwise monitor the interior of the rotatable vessel (200), for example, in order to observe particles (930) or optically quantify particles (930) separated from the surrounding fluid and sedimented in the lateral filet (220). Also in some embodiments, the rotatable vessel (200) can include structures to facilitate liquid level detection (LLD). In some of these embodiments, such structures may include carbon in order to facilitate capacitive LLD. As described herein, the rotatable vessel (200) may also be coated with certain materials. For instance, the region of sedimentation (301) on the surface of the inner walls of the lateral collection chamber (220) may have a surface structure facilitating the binding of specific particles (930).

Figure 2B:
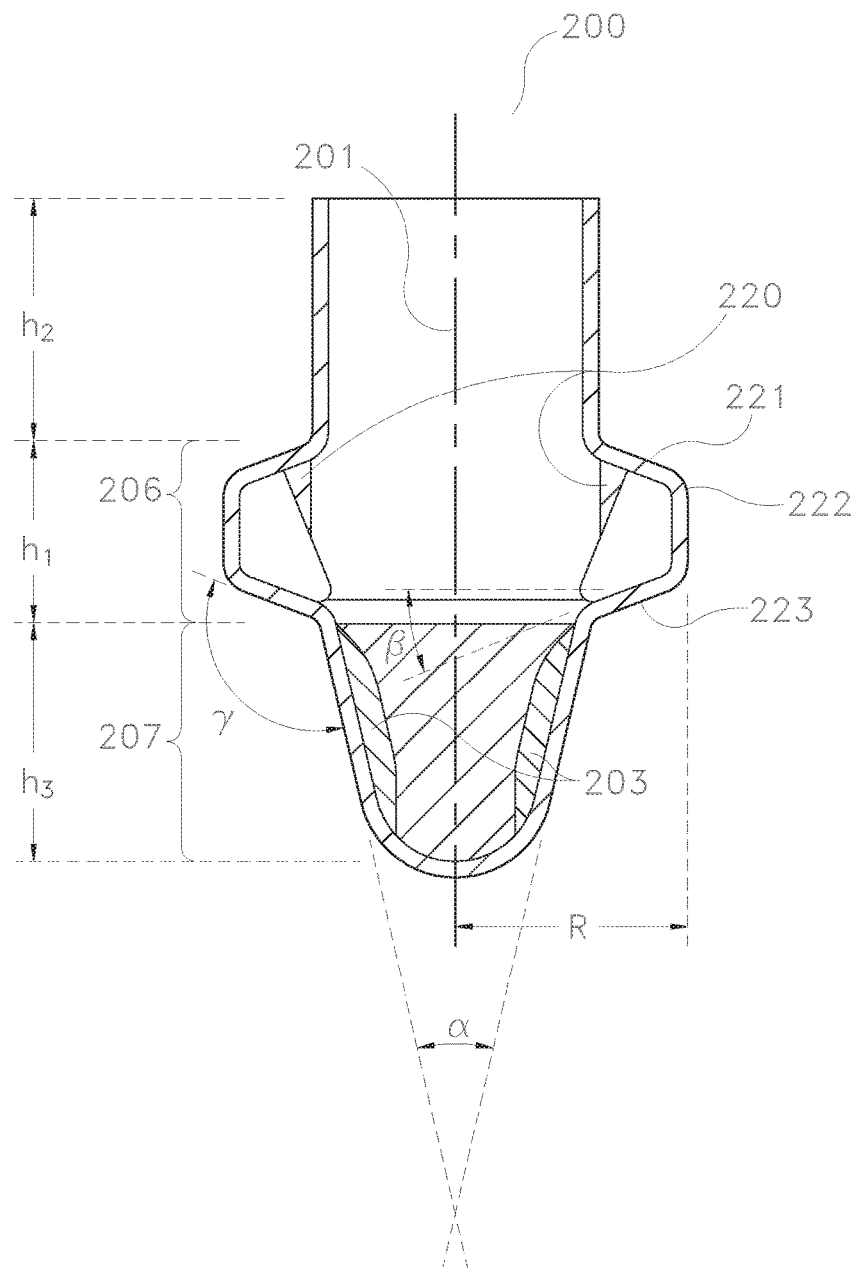

The schematic depiction in FIG. 2B shows a cross-section of a rotatable vessel (200) comparable to the one of FIG. 2A.

In this figure, the dimensions and geometry of certain embodiments of the rotatable vessel (200) are displayed. Depending on different conditions such as type of particles (930), type of sample (920), desired rate of throughput, need for parallelization, or the like, the shape and measures of the rotatable vessel (200) may be adapted. Dimensions of significance can be, for instance, h1 (height of the lateral collection chamber (220) or liquid held therein, respectively), h2 (horizontal protrusion of the lateral collection chamber (220)), h3 (height of the lower portion (207) of the rotatable vessel (200)), R (maximum radius of the intermediate portion (206)), and the volume Vmax(collection chamber) of the lateral collection chamber (220) or of the lower portion (207), denoted Vmax(lower). Similarly, some angles may be varied according to the respective application. Among those angles are a (between the cross-sectional tangents of the opposing tapered walls of the lower portion (207) at their intersection), 13 (the lateral collection chamber (220) of this embodiment can have an upper wall, a lower wall, and an intermediate wall with β being the angle between the lower wall and the virtual line perpendicular to the longitudinal axis (210)), and y (outer angle between the lower wall of the lateral collection chamber (220) and the wall of the lower portion (207) of the rotatable vessel (200)). Table 1 displays a selection of suitable values, whereby other values are possible.

TABLE 1

| | Description | Embodiment 1 | Embodiment 2 | Embodiment 3 | Unit |
|---|---|---|---|---|---|
| | | Range | | | |
| α | angle between walls of lower portion | 20 to 160 | 25 to 120 | 30 to 90 | ° |
| β | angle between lower wall of collection chamber and perpendicular line of longitudinal axis | 10 to 80 | 20 to 70 | 30 to 70 | ° |

TABLE 1-continued

| | Description | Embodiment 1 | Embodiment 2 | Embodiment 3 | Unit |
|---|---|---|---|---|---|
| γ | angle between lower wall of collection chamber and wall of lower vessel portion | 100 to 250 | 110 to 225 | 120 to 200 | ° |
| h1 | height of (liquid in) lateral collection chamber | 0.5 to 30 | 1 to 15 | 2 to 12 | mm |
| h2 | horizontal protrusion of lateral collection chamber | 0.05 to 15 | 0.05 to 10 | 0.05 to 7 | mm |
| h3 | height of lower portion | 1 to 100 | 2 to 50 | 2 to 40 | mm |
| R | maximum radius of intermediate portion | 2 to 100 | 5 to 80 | 7 to 50 | mm |
| Vmax (collection chamber) | maximum volume of lateral collection chamber | 0.02 to 100 | 0.1 to 10 | 0.2 to 5 | ml |
| Vmax (lower) | maximum volume of lower portion | 0.02 to 100 | 0.1 to 10 | 0.2 to 5 | ml |

Figure 2C:
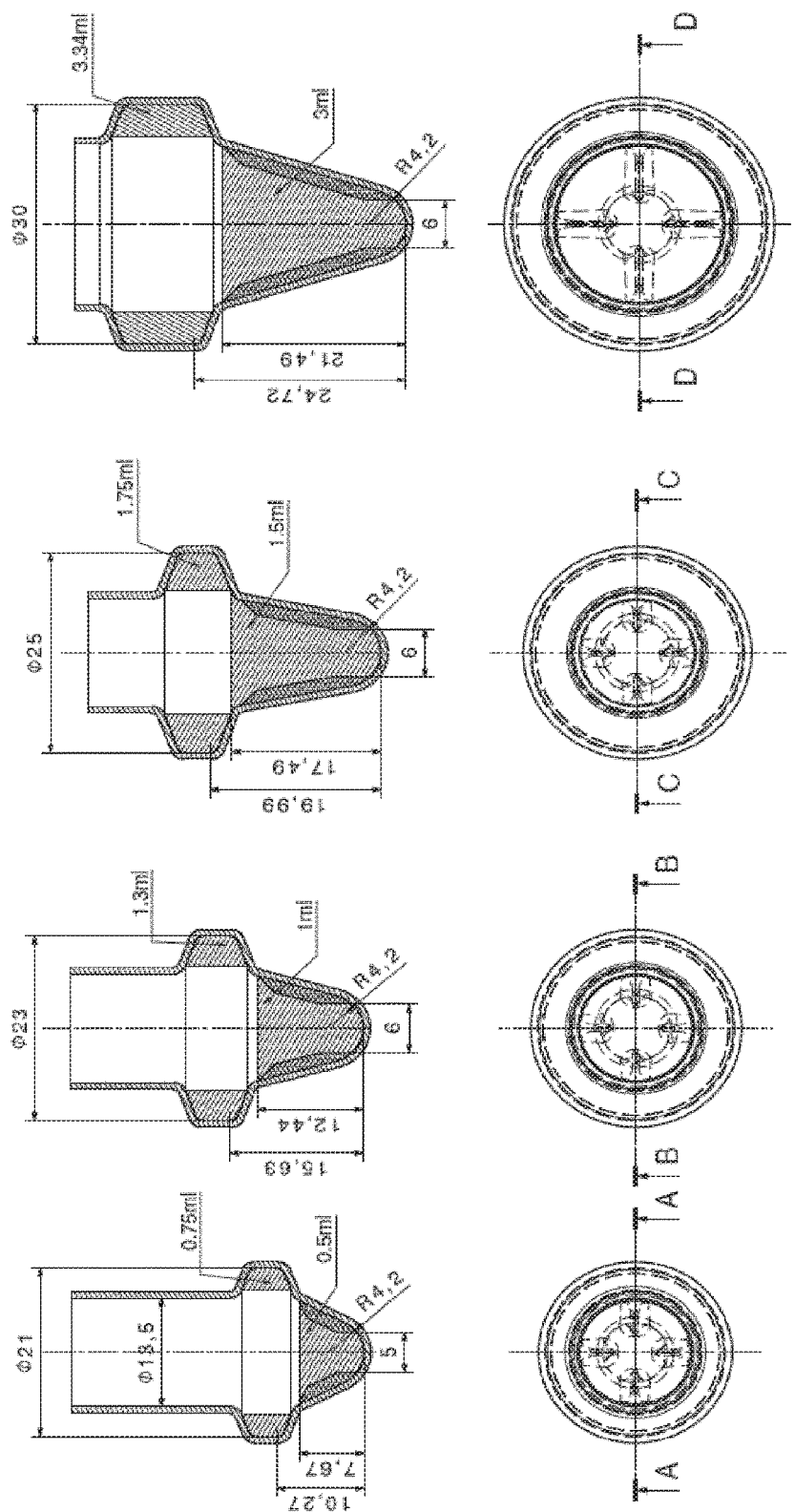

Four specific variations of the rotatable vessel (200) holding between 0.5 ml and 3 ml are shown in FIG. 2C. As in FIG. 2A, the rotatable vessel (200) is depicted as a vertical cross-section (upper drawing) and as a top view (lower drawing). The drawings illustrate exemplary embodiments addressing various target processing volumes from 0.5 ml (A) to 3 ml (D).

Figure 2D:
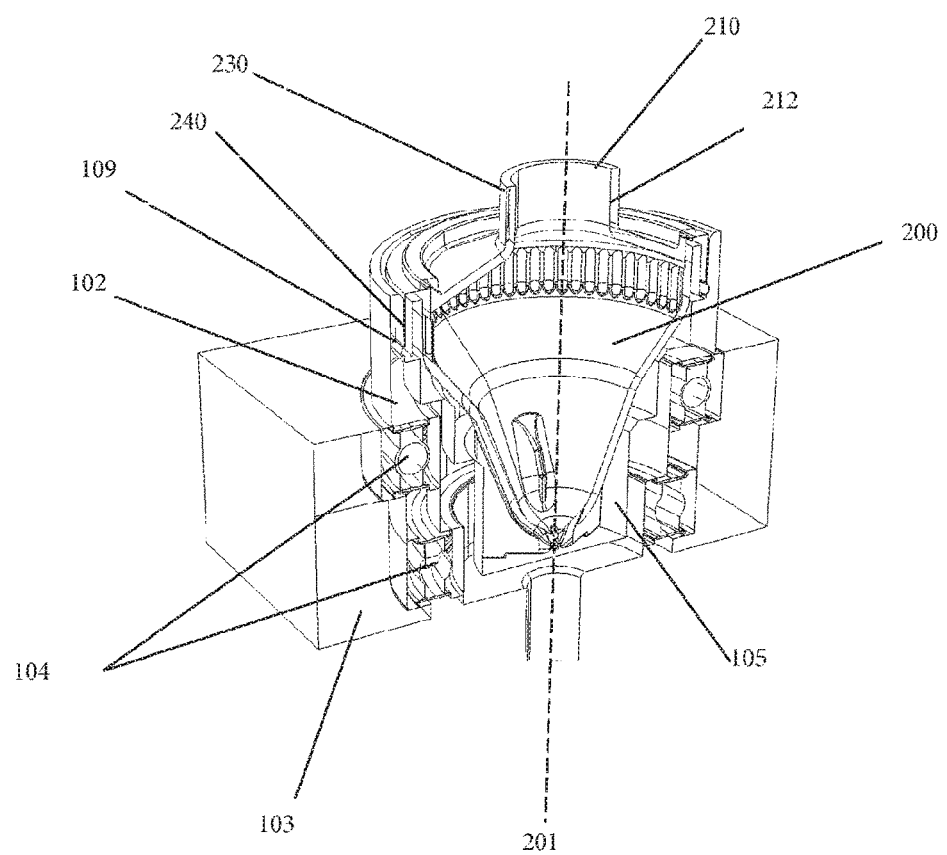

A cross-sectional view of a rotatable vessel (200) held in a dedicated receptacle (105) of a rotor (102) moving it about its longitudinal axis (201) is provided in FIG. 2D. The rotatable vessel (200) depicted herein includes a chimney (212) to reduce evaporation through the top opening (210). The chimney (212) can also provide a handle (230) suitable for a robotic gripper, such that the rotatable vessel (200) may be readily moved within the automated system (1). The rotor (102) and the rotatable vessel (200) can have lock mechanisms interacting with each other to maintain the rotatable vessel (200) stably in the rotor (102). The rotor (102) can have a lock (109) fitting to its counterpart (240) comprised by the rotatable vessel (200). The respective locking may, for instance, be effected via force-fit or press-fit or other suitable mechanisms. In this context, the locking may be reversible or irreversible. In embodiments where the locking is reversible, the rotatable vessel (200) may be readily removed from the rotor (102) if needed without being damaged. The rotor (102) itself can be held by a console (103), while bearings (104)—in the depicted embodiment ball bearings—can provide guidance and reduce friction for the rotation of the rotor (102) in relation to the console (103).

Figure 2E:
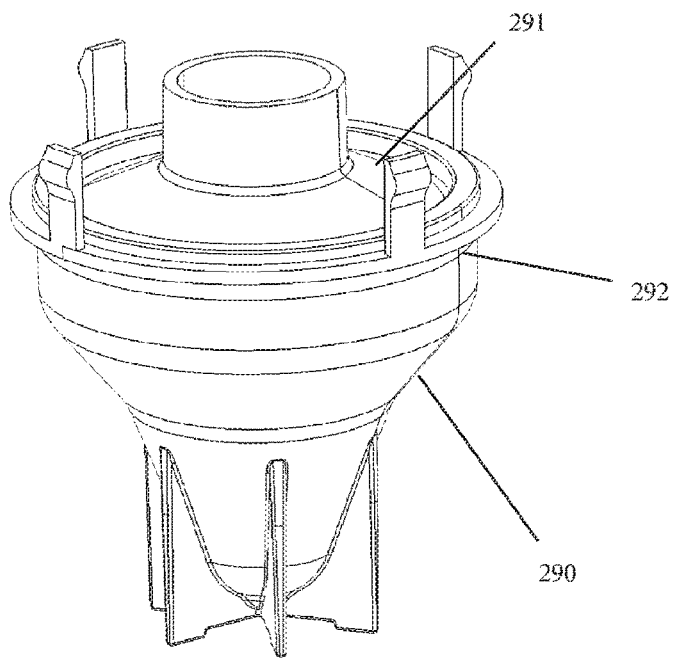

FIG. 2E shows a perspective view of an embodiment of the rotatable vessel (200) described herein wherein the vessel (200) can be assembled by joining two parts together, a lower (290) and an upper (291) part. Such parts may be produced separately by injection molding and joined thereafter, by techniques such as force-fit, laser-joining, ultrasound-joining, gluing with a UV-curable adhesive, or the like. The assembly of the single injection-molded parts of the rotatable vessel (200) may be finalized by creating a sealing rim (292). For reasons of quality control of the tightness of an assembled rotatable vessel (200), it can be controlled by application of pressurized air or another gas. Alternatively the rotatable vessel (200) may also be produced by stretch blow molding, or the like.

Figure 2F:
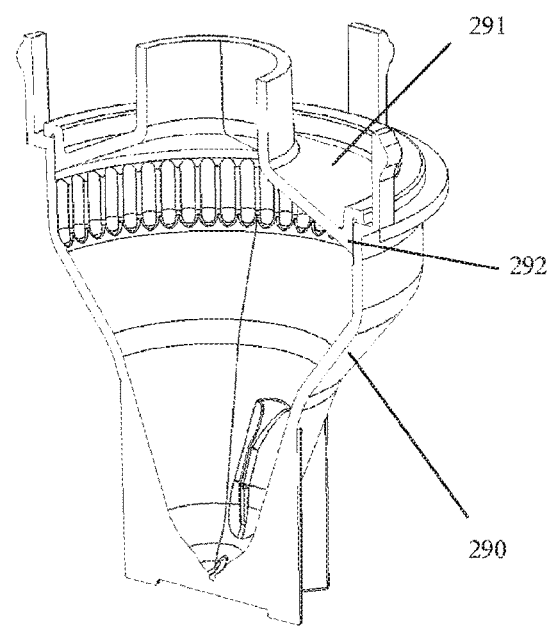

FIG. 2F shows the respective cross-section of the rotatable vessel (200) of FIG. 2E. The rotatable vessel (200) may be made of any material compatible with the processing of the particles in question. For example, in the case of processing cells, a suitable material may be polypropylene. In case of production by stretch blow molding, PET may be used.

Figure 3A:
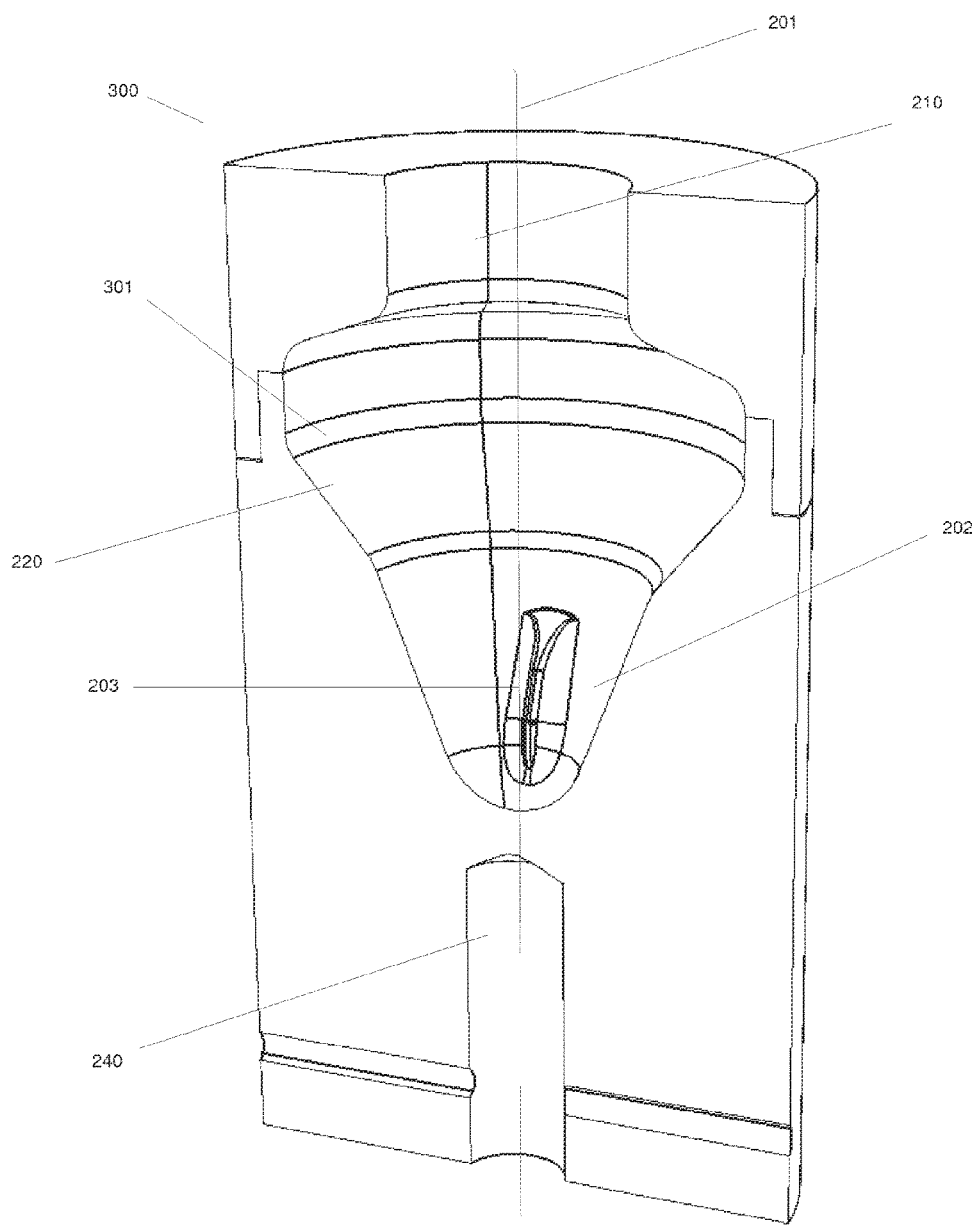
FIGS. 3A-D illustrate cross-sectional views of the rotatable vessel according to an embodiment of the present disclosure.

FIG. 3A displays a vertical cross-section of a specific embodiment of the rotatable vessel (300) described herein. In this embodiment, the mechanical lock (240) of the rotatable vessel (300) can be a recess below its bottom portion. The recess (240) may interact with its counterpart comprised by the rotor (102). The baffle (203) extending towards the inner space (202) of the lower portion (207) of the rotatable vessel (300) can contribute to moving the liquid, as described above. The rotatable vessel (300) can have a region of sedimentation (301) located at the inner wall of the lateral collection chamber (220), where particles (930) can sediment due to centrifugal force upon rotating the rotatable vessel (300) about its longitudinal axis (201). The region of sedimentation (301) can be, in some embodiments, liquid-tight, such that no liquid is spilled.

In some embodiments of the rotatable vessel (300) described herein, the region of sedimentation (301) the inner surface of the lateral collection chamber (220) can have a retention structure for retaining the particles contained in the liquid biological sample (920).

The "retention structure" may imply, in some embodiments, that the inner surface of the region of sedimentation (301) can be polished, micro-structured, can have a predefined roughness, or carry a coating or has been treated otherwise, such as plasma-treated, sand-blown, or sputtered in order to hold and release the particles (930) under predefined conditions. In some embodiments, the surface roughness can be in a range of about 0.25 to about 100 μm, which can be especially suitable in embodiments where the particles (930) are blood cells such as white blood cells. In some embodiments, the surface of the region of sedimentation (301) can have a roughness from about 0.5 to about 50 μm, or from about 1 to about 25 μm. The material of the region of sedimentation (301) can be selected to hold and release cells under predefined conditions. Suitable materials can comprise, among others, polypropylene, polyethylene and polystyrene, acrylonitrile butadiene styrene (ABS), stainless steel such as 316L, or other materials. These materials can be especially advantageous in embodiments where the particles (930) are blood cells such as white blood cells.

In some embodiments, the retention structure can include a metal-oxide or silica surface. Silicon dioxide surfaces such as glass surfaces may be used to bind nucleic acids in the presence of chaotropic agents. Therefore, in some embodiments of the rotatable vessel (300) described herein, the retention structure can comprise a silicon dioxide surface, which can, in some embodiments, be a glass surface. In such embodiments, the surface of the rotatable vessel's (300) inner walls outside of the lateral collection chamber (220) may be made of a different material in order to achieve selective binding of the particles (930) to the retention surface of the lateral collection chamber (220) under chaotropic conditions. This embodiment can allow for the application of the technology based on Boom et al. (EP 389063) without the need for classical centrifugation with bottom sedimentation, the need for silica filter devices, or the need for magnetic beads with glass surfaces.

Also in some embodiments, the retention structure can comprise surface molecules for binding the particles (930) contained in the liquid biological sample (920).

In some embodiments, such surface molecules may be nucleic acid capture probes, oligo- or poly(dT)-strands for binding mRNA, protein A for binding the Fc parts of immunoglobulins, Fab fragments of antibodies for binding specific proteins, nickel for binding histidine tags, streptavidin or biotin, integrins, adhesins, or other cell-surface molecules, or the like. The retention structure may, for instance, include a streptavidin coating which can be functionalized "on demand" such as by exposure to a biotinylated probe specific for the respective biological target. In some embodiments, the particles (930) can be cells exposing cell surface molecules on the outer layer of their membrane, such that specific cells may be captured by the surface molecules of the retention structure of the lateral collection chamber (220). For example, for blood samples, suitable antibodies specifically binding to cell surface antigens of leucocytes, erythrocytes, monocytes are known to people skilled in the art (for example, CD2/CD3 for T cells, CD14 for monocytes, CD15 for granulocytes and monocytes, CD16 for macrophages, CD36 for platelets, monocytes and macrophages, CD45 for leucocytes, or the like). For such purposes, those antibodies or other binding molecules may be immobilized on the surface of the region of sedimentation (301) of the inner wall of the lateral collection chamber (220) by methods known to the skilled person. Methods of immobilization may include linker molecules and include covalent and/or non-covalent bonds. Likewise, in case the particles (930) are bacteria, the surface may be coated with antibodies specific to bacteria or a specific genus or species thereof.

Other retention structures are possible, some of which are described herein.

Figure 3B:
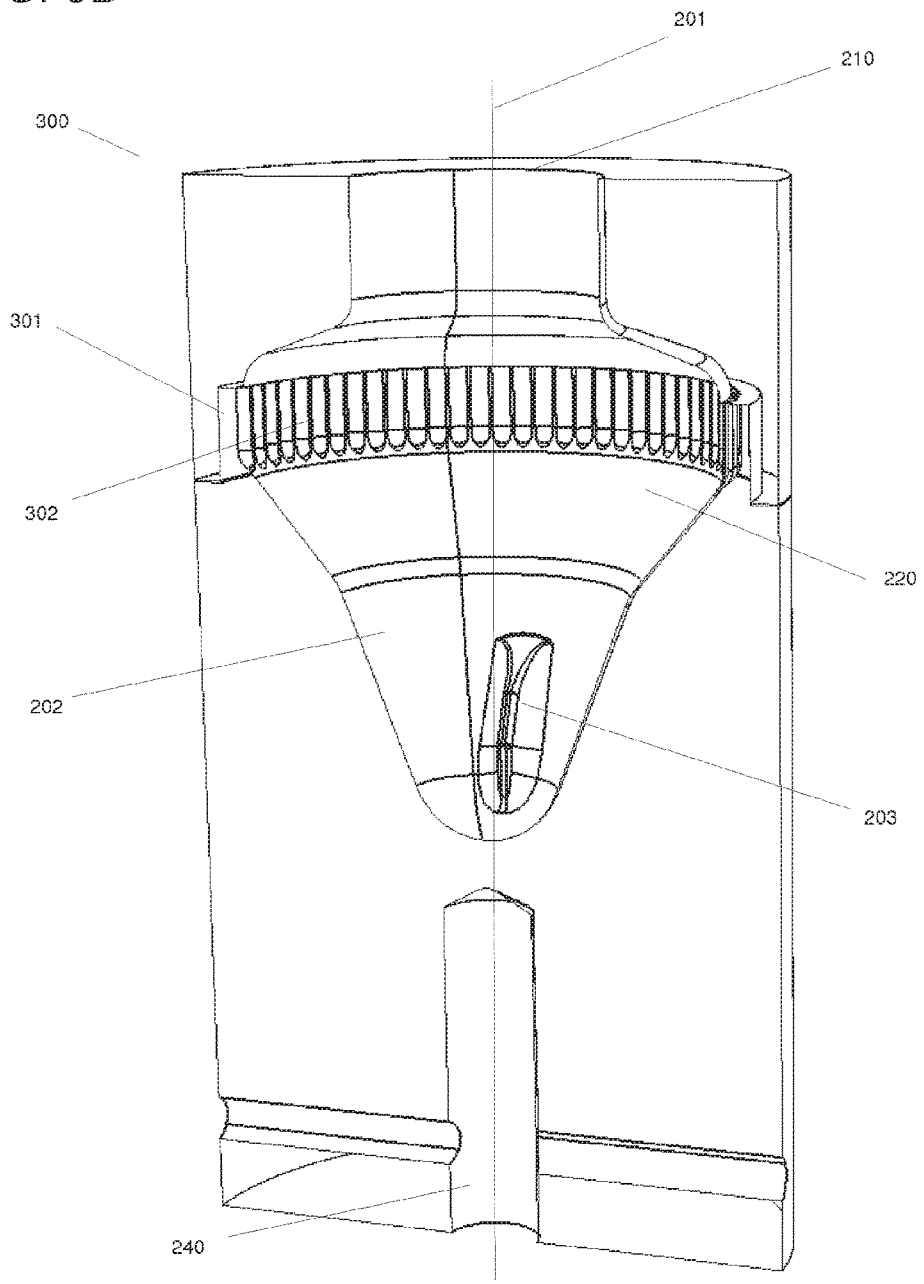

FIG. 3B shows an embodiment of the rotatable vessel (300) similar to the one shown in FIG. 3A. In the embodiment depicted in this figure, vertical grooves (302) can be present in the region of sedimentation (301) within the lateral collection chamber (220), contributing to retaining the particles sedimented during and after sedimentation by protecting them mechanically from unwanted re-suspension while the rotation is decelerated or stopped.

Hence, in some embodiments of the rotatable vessel (300) described herein, the retention structure can comprise vertical grooves (302). The vertical grooves (302) can be, in some embodiments, of sufficient size to hold at least one particle (930). In some embodiments, the dimensions can be a depth of about 2 to about 2000 μm, about 5 to about 1000 μm, or about 20 to about 300 μm, a width of about 50 to about 1000 μm, and a pitch of about 0 to about 500 μm.

In embodiments where the particles (930) are located within a groove (302) during or after rotation of the rotatable vessel (300) about its longitudinal axis (201), the particles (930) can be at least partly shielded from the flow of the surrounding liquid, thus reducing the force pulling the particles (930) away from the retention structure. This shielding can be promoted by the fact that the grooves (302), in this embodiment, can be vertical and therefore mostly orthogonal to the direction of rotational flow of the rotating liquid while accelerating or decelerating the rotatable vessel (300). Additionally, the vertical grooves (302) may include surface molecules for binding the particles contained in the liquid biological sample (920), as described herein. On the other hand, the grooves (302) can be arranged to still release the particles upon sufficient rotational acceleration or deceleration.

Figure 3C:
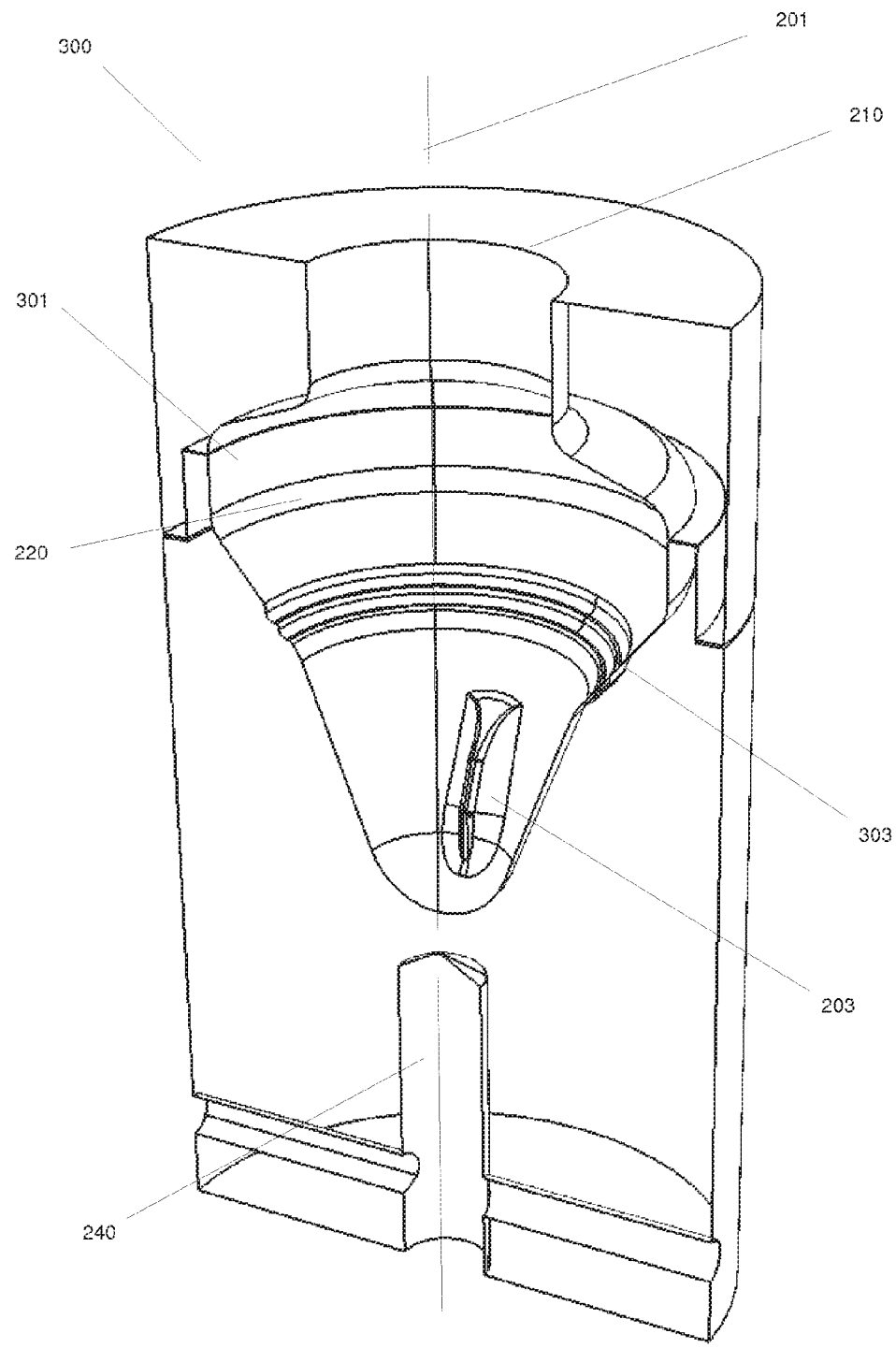

The embodiment shown in FIG. 3C features a rotatable vessel (300) having ring-shaped horizontal grooves (303) as a retention structure. These grooves (303) can extend around the inner wall of the lower part of the lateral collection chamber (220). In some embodiments, the ring-shaped horizontal grooves (303) can be located at the interface between the intermediate portion (206) and the lower portion (207) of the rotatable vessel (300). In some embodiments, there may be only one groove (303), in other embodiments; there can be multiple grooves (303). Generally, this structure can contribute to retain the particles (930) in the lateral collection chamber (220) of the intermediate portion (206), since they can pose a mechanical obstacle for the particles (930), but less so for the surrounding liquid. Hence, when the rotational movement of the rotatable vessel (300) about its longitudinal axis (201) stops, the liquid may flow back to the lower portion (207) following gravity, while the particles (930) are retained in the lateral collection chamber (220) with the help of the ring-shaped horizontal grooves (303) and, in some embodiments, further retention structures.

Figure 3D:
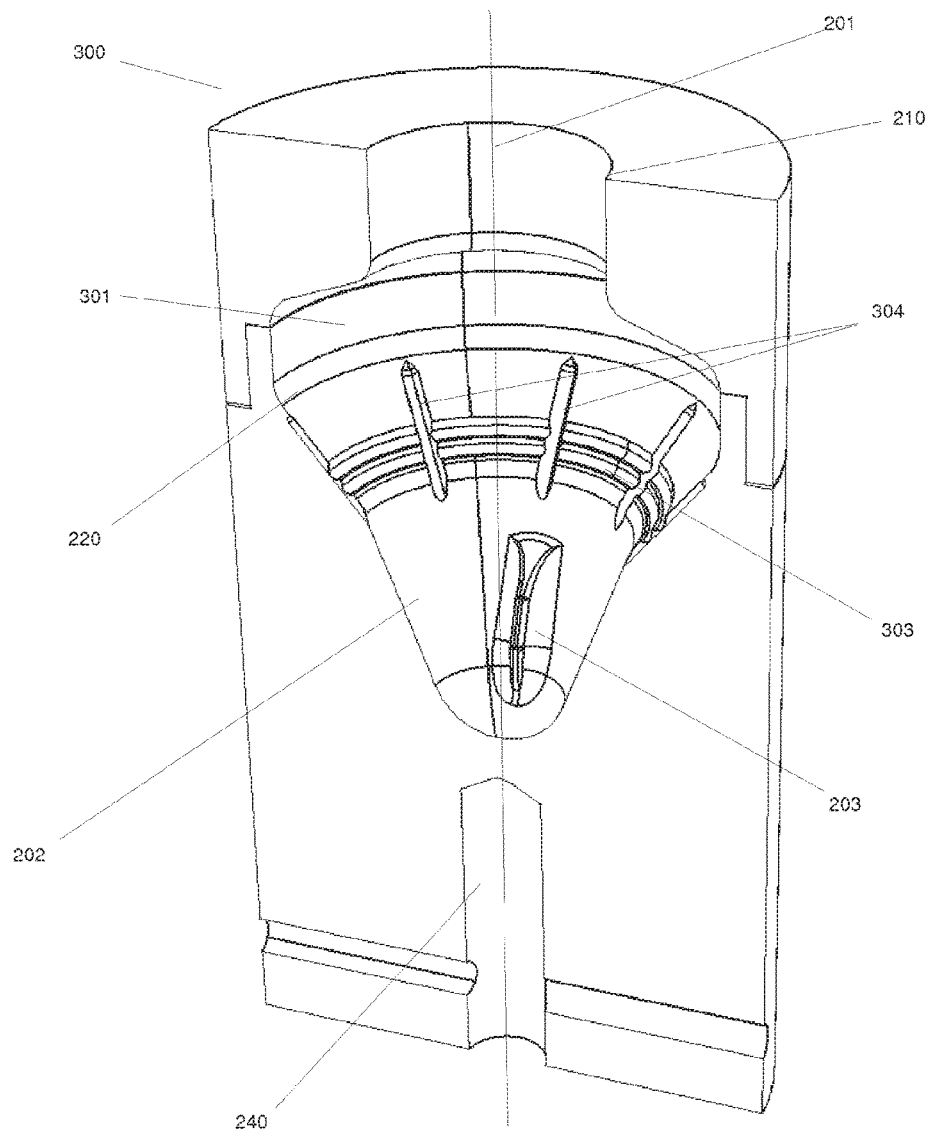

FIG. 3D shows an embodiment of the rotatable vessel (300) having the features shown in FIG. 3C, and additionally displaying vertical capillary grooves (304) extending from the lateral collection chamber (220) of the intermediate portion (206) to the lower portion of the rotatable vessel (207). The vertical capillary grooves (304) can thus be oriented substantially parallel to the gravitation-driven direction of flow when the rotatable vessel (300) is resting. This additional measure can facilitate the complete removal of liquid from the lateral collection chamber (220), while particles (930) are retained therein.

Rotatable Vessel having a Burst Valve

Figure 4:
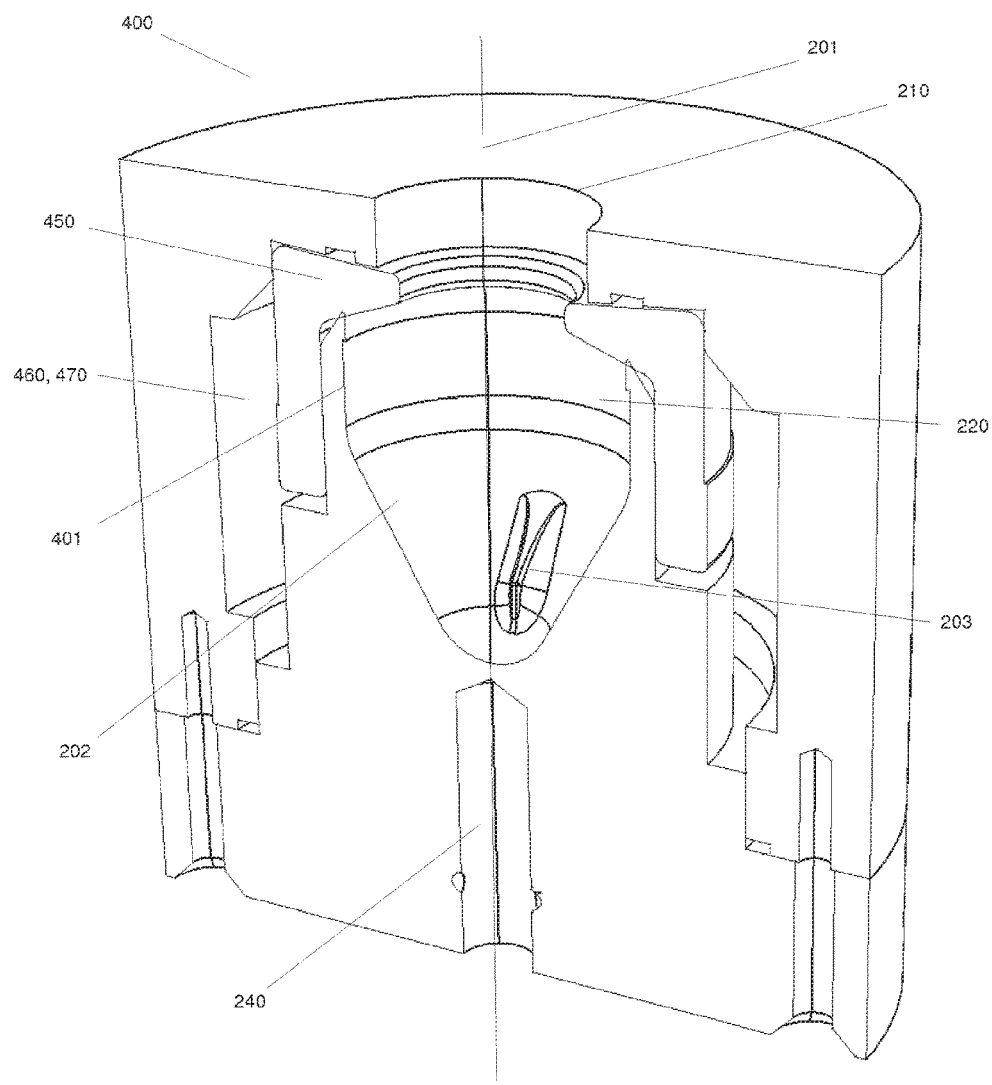
FIG. 4 illustrates a cross-sectional view of a rotatable vessel having a burst valve according to an embodiment of the present disclosure.

FIG. 4 depicts another embodiment of the rotatable vessel (400) described herein, involving a burst valve (450). As before, the view displayed here is a vertical cross-section of the rotatable vessel (400). As described in the context of FIGS. 3A-D, the current embodiment can also include a region of sedimentation (401) at the inner wall of the lateral collection chamber (220), a longitudinal axis (201), a top opening (210), a baffle (203), a lock (240) for interaction with the rotor (102), and a longitudinal axis (201) about which the vessel (400) is rotatable. The rotatable vessel (400) may also include any of the additional features described above, such as vertical or horizontal grooves, or capillary grooves between lateral collection chamber (220) and lower portion (207), and the like.

Another feature of the intermediate portion (206) of the rotatable vessel (400) shown in the present depiction can be a burst valve (450) in fluid communication with the lateral collection chamber (220) on one side, and a peripheral zone (460), wherein peripheral can be understood with respect to the longitudinal axis (201). The burst valve (450) can be adapted and arranged to drain the liquid from the lateral collection chamber (220) when centrifugal force or rotational speed exceed a critical value, while being liquid tight below that value.

In such an embodiment, it may not be necessary to withdraw any supernatant from the rotatable vessel (400) by a pipettor (910). While the pipettor (910) may still be used to introduce the liquid biological sample (920) or other liquids into the rotatable vessel (400) or other components of the automated system (1), the burst valve (450) may be employed to remove the liquid from the rotatable vessel (450) while retaining the particles (930) contained therein. For instance, a rotatable vessel (400) may be rotated about its longitudinal axis (201) at a first rotational speed, wherein the centrifugal force can be sufficient to sediment the particles (930) in the region of sedimentation (401) of the lateral collection chamber (220), while the surrounding liquid can also be pressed into the collection chamber (220). At a second rotational speed higher than the first one, the liquid may be subjected to a centrifugal force exceeding a critical value, such that the liquid can be pressed through the burst valve (450) whose retaining capacity can be exceeded such that the valve (450) can "burst". In this context, to "burst" may not be necessarily mean irreversible rupture of the valve (450). In some embodiments, the valve (450) can rather allow liquid to pass through itself when the liquid applies a critical pressure on it, not affecting its capability to withhold liquid below that critical pressure in a possible subsequent experiment. This embodiment can contribute to the ease of automation when using a rotatable vessel (400) described herein. Any supernatant may be removed from the rotatable vessel (400) by the same method that can be used to sediment the particles (930). This embodiment can also reduce the required time for automated particle processing and thus potentially increases sample throughput. In some embodiments, only the liquid, but not the particles—which can remain in the lateral collection chamber (220)—can be pressed against the burst valve (450) at the second rotational speed. In such embodiments, the burst valve (450) may not be exposed to the potential risk of clogging due to particles (930) pressed against it or its openings.

In some embodiments of the rotatable vessel (400) described herein, the burst valve (450) can be a hydrophobic valve "bursting" upon application of a certain pressure caused by centrifugal force and hydrostatic pressure, as described above. The burst valve (450) may, in some embodiments, comprise hydrophobic porous plastic, a hydrophobic porous membrane, a membrane with laser-drilled holes with diameters in a range of about 5 to about 50 um, wherein the hydrophobic burst valve (450) can be formed between two pieces of plastic joined to each other.

Also in some embodiments, the burst valve (450) can be a spring-loaded valve, opening upon application of a critical pressure caused by centrifugal force to the spring or sealant of the valve (450).

In further embodiments, the burst valve (450) can be an elastomeric structure which can elongate upon the application of a critical pressure caused by centrifugal force and thus release an opening.

In the embodiment shown in FIG. 4, the rotatable vessel (400) can also include a peripheral zone (460) located outside the inner space of the rotatable vessel (400). In this embodiment, the burst valve (450) may let the liquid pass upwards through the top opening (210) of the rotatable vessel (400), such that the liquid can flow into the peripheral zone (460). From there, the liquid may be collected and further processed or discarded.

In some embodiments, the rotatable vessel (400) may comprise a waste chamber or container (470) which may, for instance, be in fluid communication with the peripheral zone (460). In some embodiments, such a waste chamber or container (470) may be spatially separated from the rotatable vessel (400). In embodiments including a waste chamber or container (470), any liquid separated from the particles (930) in question may be conveniently removed and discarded within the automated system (1). Such a container (470) may be retrieved from the automated system (1) and emptied or replaced routinely or whenever needed.

Rotatable Vessel with a Peripheral Filter

Figure 5:
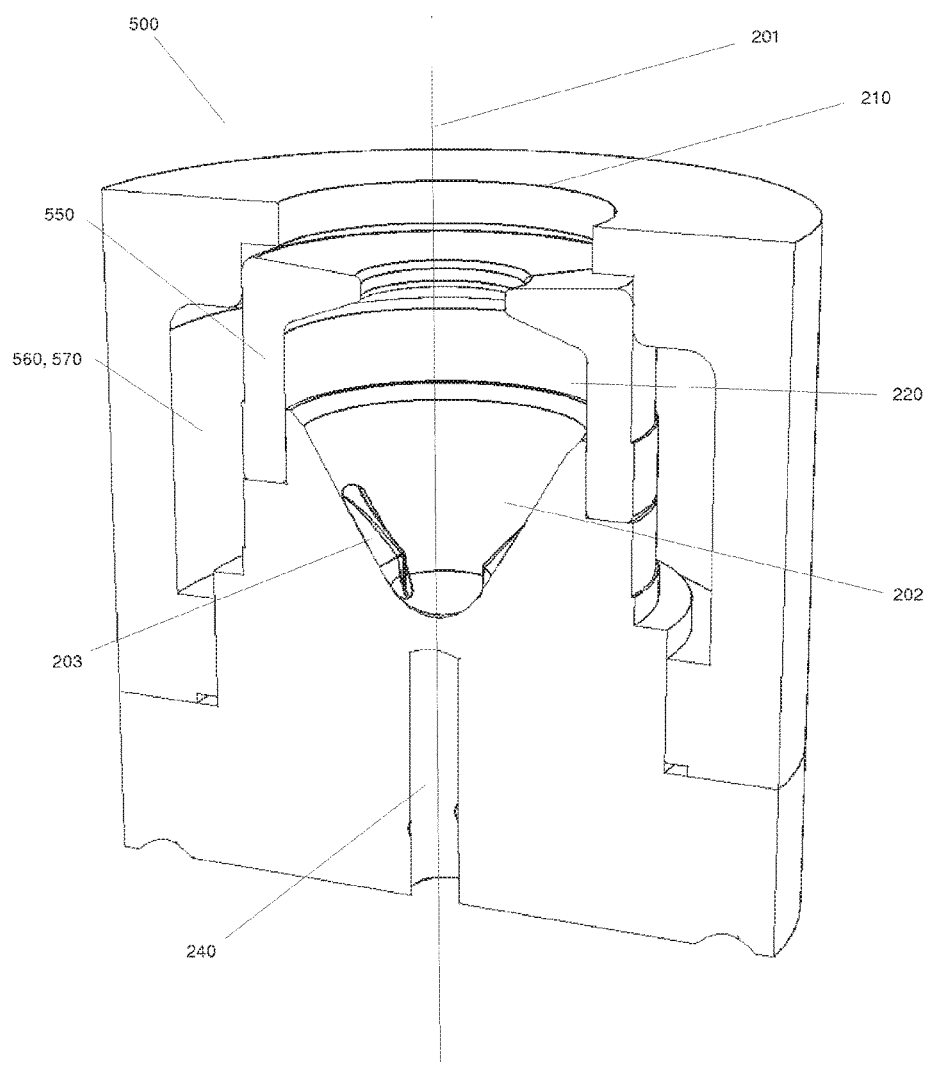
FIG. 5 illustrates a cross-sectional view of a rotatable vessel having a peripheral filter according to an embodiment of the present disclosure.

FIG. 5 shows an embodiment of the rotatable vessel (500) using a peripheral filter (550) at the wall of the lateral collection chamber (220). The filter (550) in this embodiment can hold back the particles (930) sedimented in the lateral collection chamber (220) while letting the liquid pass through the wall of the collection chamber (220). In some embodiments, the peripheral filter (550) can be hydrophobic. Also in some embodiments, the peripheral filter (550) can have a burst pressure following a similar principle as the burst valve (450) described supra. In the present context, the burst pressure can be a value applicable for the liquid that passes through the peripheral filter when the applied pressure exceeds that critical value. The particles, on the other hand, can be retained by the peripheral filter (550) also above this critical or "burst" pressure. As in the embodiment shown in FIG. 4, the rotatable vessel (500) of the present embodiment may also include a peripheral zone (560) for collecting the liquid expelled from the inside of the rotatable vessel (500) through the peripheral filter (550).

The embodiment depicted in FIG. 5 may also abolish the need of a dedicated system like a pipettor (910) to remove the liquid from the inside of the rotatable vessel (500).

Figure 6A:
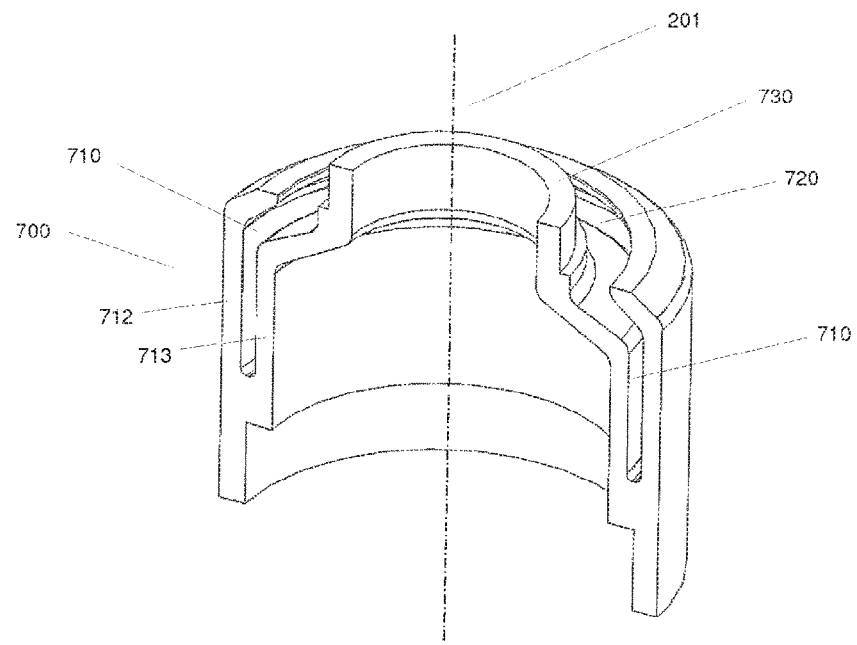
FIGS. 6A-G illustrate perspective views of a rotatable vessel having an annular peripheral chamber for imaging according to an embodiment of the present disclosure.

Rotatable Vessel with an Annular Peripheral Chamber for Optically analyzing Particles FIG. 6A is a depiction of an embodiment in which the rotatable vessel (700) comprises an annular peripheral chamber (710) that may be filled via a slit-like opening (720) and serves as a chamber for the imaging of particles (930), for instance, with the help of a scanner (600) and imaging optics (640) as described herein. The peripheral chamber (710) of the depicted embodiment can have an annular shape and can be located in relatively close vicinity to the vessel's (700) side wall. The horizontal depth of the chamber (720) can be adapted to the needs. It can be generally be larger than the diameter of the particles (930) to be analyzed. Generally, the depth of the chamber can be adapted to harbor a target volume of particle suspension. In some cases, it can be advantageous that the particles (930) to be analyzed, when sedimented to the outer wall of the peripheral annular chamber (710), are sufficiently separated from each other such that they do not or only rarely overlap. The particle density can be a result of the particle concentration and the height of the chamber (710).

Alternatively or additionally, the rotatable vessel (700) can be centrifuged and the particles (930) can thus be sedimented at the peripheral wall of the chamber (710). In this embodiment, the liquid may not be retrieved and thus separated from the particles (930). In fact, the rotatable vessel (700) may be devoid of a lower portion for holding the liquid when the vessel (700) is resting. It can be advantageous for imaging of the particles (930) to maintain the liquid within the peripheral chamber (710) following centrifugation. In such embodiments, the media immediately surrounding the centrifuged particles (930) can be optically homogeneous and well-defined. This can be advantageous as compared to embodiments where particles (930) are centrifuged in other vessels described herein, in which the liquid can be collected in the lower portion after stopping the rotation. In the latter case, a liquid film can still be attached to the particles along with its interface to the surrounding air may be more demanding to optically analyze. Further, leaving particles (930) such as cells in the liquid of the chamber (710) of the rotatable vessel (700) of the current embodiment can contribute to preserving the particles' (930) integrity and protects potential staining from oxidation, photo bleaching or from drying out Hence, a rotatable vessel (700) for optically analyzing particles (930) contained in a liquid biological sample (920) is presented. The rotatable vessel (700) can comprise a longitudinal axis (201) about which the vessel (700) is rotatable, a transparent outer wall (712), an upper portion (205) comprising a top opening (210) for receiving the liquid biological sample (920) comprising the particles (930), and an intermediate portion (206) located below the upper portion (205). The intermediate portion (206) can comprise an annular peripheral chamber (710) for holding the liquid while the rotatable vessel (700) is rotating. The annular peripheral chamber (710) can comprise on the surface of its inner wall a region of sedimentation (301) for the particles (930) contained in the liquid biological sample (920). The annular peripheral chamber (710) can be fluidically connected to the top opening (210).

The transparent outer wall (712) can allow the transmission of light of any wavelength required for particle (930) analysis, such as light for fluorescence excitation, light originating from fluorescence emission, or for transmission of reflected light. When detecting DNA by absorbance in a transmission mode, the material in some embodiments can permit the transmission of UV. The inner wall (713) may either also be transparent, particularly in the context of transmission-based detection, or it may be opaque and/or of any color, in some embodiments black.

The rotatable vessel (700) may include orientation marks in order to determine locations in the device. Such orientation marks may be, for example, vertical grooves applied to the inner surface (711) or parts of the inner surface (711). Narrow mechanical tolerances may facilitate autofocusing methods.

Further, to enhance compatibility of the rotatable vessel (700) of this embodiment with bright field illumination or transmission and/or fluorescence detection, the center of the vessel (700) may, for example, include an opening. The vessel (700) may further include an interface (730) for a robotic manipulator such as a gripper, as in the depicted embodiment. The annular peripheral chamber (710) may also contain one or multiple baffles.

Figure 6B:
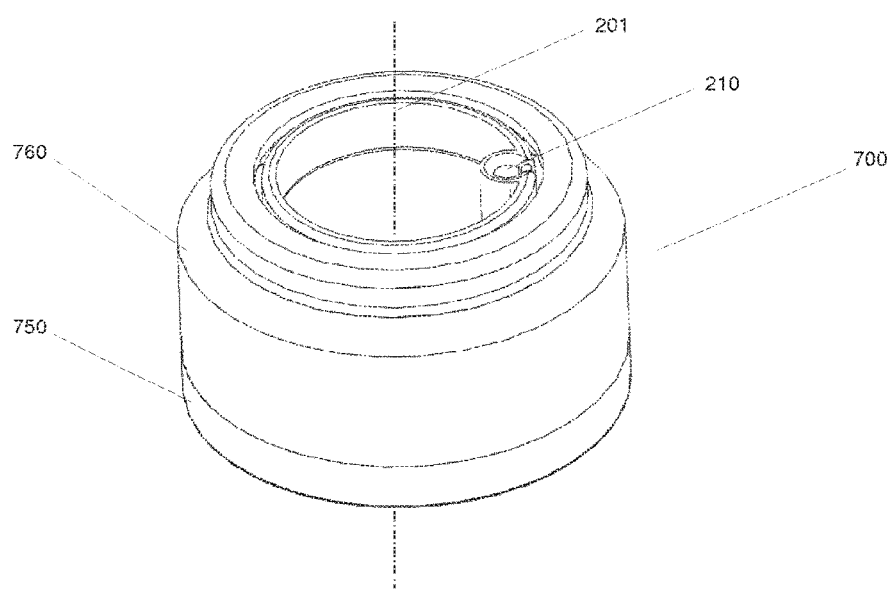
Figure 6C:
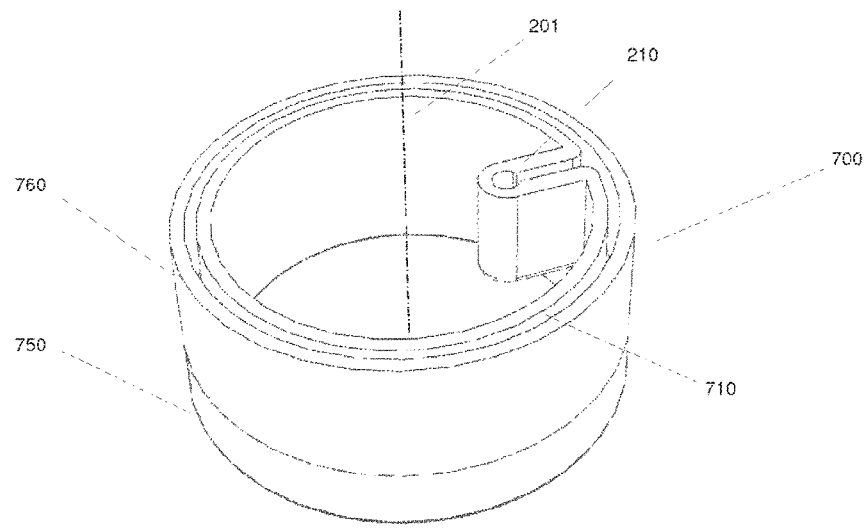

FIG. 6B shows a perspective view of a rotatable vessel (700) with an annular peripheral chamber (710), while FIG. 6C depicts a horizontal cross-sectional view thereof. The top opening (210) for introducing the liquid sample into the annular peripheral chamber (710) is visible in these figures, along with the lower (750) and the upper (760) part from which the vessel (700) can be produced.

Figure 6D:
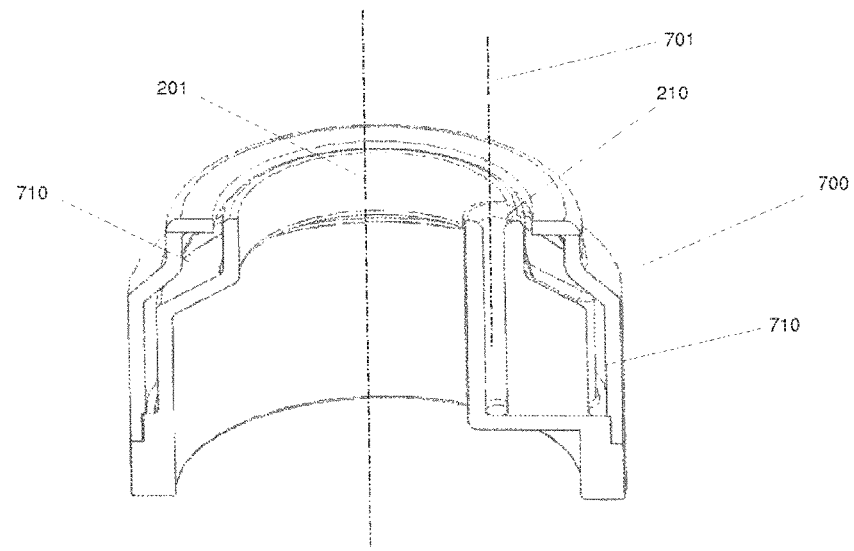

FIG. 6D, providing a perspective view of a vertical cross section of the rotatable vessel (700), shows the annular peripheral chamber (710) and its fluidic connection with the top opening (210) in greater detail. Following the filling axis (701), for example, a pipetting needle may in some embodiments be introduced into the opening (210). In some embodiments, the needle may be inserted at a substantial depth of the opening (210) or all the way to the bottom of the opening (210), thus avoiding substantial formation of air bubbles within the fluid samples upon bottom-up filling of the annular peripheral chamber (710). The opening (210) may also serve as an interface for withdrawing the liquid from the rotatable vessel (700) again.

Figure 6E:
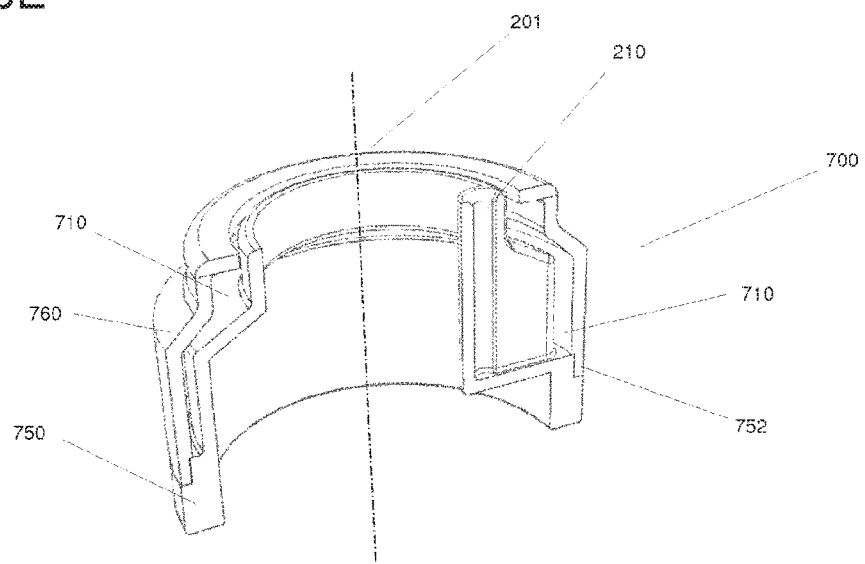
Figure 6F:
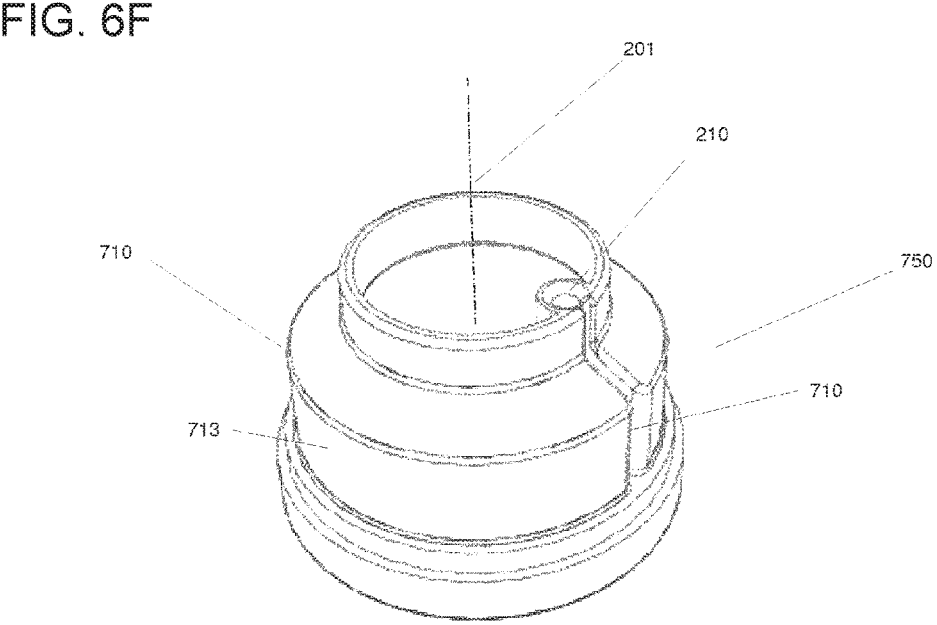

As shown in the perspective vertical cross-sectional view of FIG. 6E, the rotatable vessel (700) may be made by an assembly of two injection molded parts, a lower (750) and an upper (760) part. After production of these single parts, they may be joined at the section (752) by clamping, laser sealing, ultrasound welding, thermal fusion process, gluing, using a photo-curable adhesive, or the like. For the sake of clarity, the lower part (750) is depicted alone in FIG. 6F, before assembly with the upper part (760). The axis-near surface or inner wall (713) of the annular peripheral chamber (710) is visible in this depiction. It can be seen that the top opening (210) is, in this embodiment, formed by an invagination of the inner chamber wall (713).

Figure 6G:
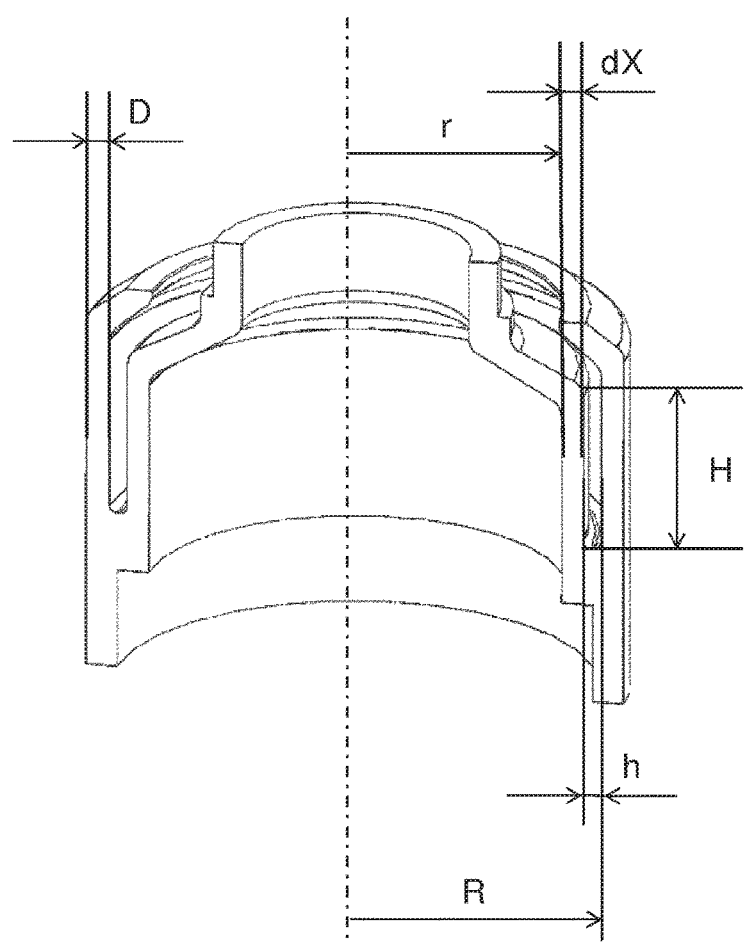

FIG. 6G, a cross-sectional side view of the rotatable vessel (700), can display exemplary dimensions of the vessel structures in conjunction with the following values.

TABLE 2

| | Description | Range | | | Unit |
| --- | --- | --- | --- | --- | --- |
| | | Embodiment 1 | Embodiment 2 | Embodiment 3 | |
| R | outer radius of vessel | 5 to 100 | 10 to 50 | 14.5 | mm |
| D | thickness of outer wall | 0.1 to 5 | 0.2 to 1.5 | 0.5 | mm |
| r | inner radius r = R-D-h-dX | 1 to 99 | 9 to 40 | 12 | mm |
| dX | difference of outer radius (R) minus inner radius (r) minus thickness of wall (D) minus radial depth of annular peripheral chamber (h) | 0.2 to 20 | 1 to 8 | 1.5 | mm |
| V | volume of annular peripheral chamber | 50 to 10000 | 100 to 1000 | 250 | µl |
| A | area of projection | 50 to 100000 | 100 to 10000 | 500 | mm2 |
| H | chamber height in direction of spin axis | 0.2 to 100 | 2 to 25 | 5.68 | mm |
| h | radial depth of annular peripheral chamber | 0.05 to 10 | 0.1 to 1 | 0.5 | ml |

The embodiments described herein for the rotatable vessels not having an annular peripheral chamber are also applicable to the rotatable vessel (700) having an annular peripheral chamber.

Method for Processing Particles contained in a Liquid Biological Sample

In the following, methods for processing particles contained in a liquid biological sample are described. "Processing" may mean a variety of different manipulations with potentially different objectives.

One such processing method is a method for separating particles (930) from a liquid biological sample (920). The method can comprise:

a) introducing the liquid biological sample (920) comprising the particles (930) into a rotatable vessel (200) as described herein through the top opening (210) of the rotatable vessel (200), such that the liquid is held by the lower portion (207) of the rotatable vessel (200);

b) rotating the rotatable vessel (200) about its longitudinal axis (201) at a rotational speed, wherein the liquid comprising the particles (930) is moved to the lateral collection chamber (220) by centrifugal force, and wherein the centrifugal force is sufficient to sediment the particles (930) in the region of sedimentation (301) of the inner wall of the lateral collection chamber (220); and c) decelerating and ultimately stopping the rotation of the rotatable vessel (200), wherein the liquid flows back to the lower portion (207) of the rotatable vessel (200) while at least a part of the particles (930) remain attached to the region of sedimentation (301) of the inner wall of the lateral collection chamber (220), thereby separating at least said part of the particles (930) from the liquid.

In some embodiments, the method described above can further comprise after step c):

d) withdrawing the supernatant from the rotatable vessel (200) while leaving the particles (930) in the lateral collection chamber (220).

Exploiting a scanner (600) as depicted in FIG. 1C, methods including surveillance and monitoring may be advantageously carried out.

For instance, a method for analyzing particles (930) contained in a liquid biological sample (930) is presented. The method can comprise:

a) introducing the liquid biological sample (920) comprising the particles (930) into a rotatable vessel (200) as described herein through the top opening (210) of the rotatable vessel (200), such that the liquid is held by the lower portion (207) of the rotatable vessel (200);

b) rotating the rotatable vessel (200) about its longitudinal axis (201) at a rotational speed, wherein the liquid comprising the particles (930) is moved to the lateral collection chamber (220) by centrifugal force, and wherein the centrifugal force is sufficient to sediment the particles (930) in the region of sedimentation (301) of the inner wall of the lateral collection chamber (220);

c) decelerating and ultimately stopping the rotation of the rotatable vessel (200), wherein the liquid flows back to the lower portion (207) of the rotatable vessel (200) while at least a part of the particles (930) remain attached to the region of sedimentation (301) of the inner wall of the lateral collection chamber (220), thereby separating at least said part of the particles (930) from the liquid;

d) optionally withdrawing the supernatant from the rotatable vessel (200) while leaving the particles (930) in the lateral collection chamber (220);

e) scanning the particles (930) in the lateral collection chamber (220) with a scanner (600) using light of at least one wavelength; and f) generating an analytical result based on the scanning data of step f).

Also a method for suspending particles (930) in a liquid is presented. The method can comprise:

a) rotating a rotatable vessel (200) as described before containing the particles (930) in a liquid about its longitudinal axis (201) in a first direction at a rotational speed, wherein the centrifugal force is not sufficient to sediment the particles (930) in the region of sedimentation (301) of the inner wall of the lateral collection chamber (220); and b) decelerating and ultimately stopping the rotation of the rotatable vessel (200).

In some embodiments, the method described above can further comprise after step b):

c) rotating the rotatable vessel (200) containing the particles (930) in a liquid about its longitudinal axis (201) in a second direction opposite to the first direction at a rotational speed, wherein the centrifugal force is not sufficient to sediment the particles (930) in the region of sedimentation (301) of the inner wall of the lateral collection chamber (220); and d) decelerating and ultimately stopping the rotation of the rotatable vessel (200).

In some embodiments of the method for suspending particles (930) in a liquid, step a) is preceded by adding a liquid to the rotatable vessel (200) as described herein through its top opening (210). Such liquid may be any liquid suitable for re-suspending the particles (930) in question.

The sequence of steps a) and b), of c) and d), or a) through d) may be repeated one or more times if required to increase the effect of (re)suspension.

In some embodiments, the method for processing particles (930) can be a method for separating particles (930) from a liquid biological sample (920) and re-suspending them in a secondary liquid. The method can comprise:

a) introducing the liquid biological sample (920) comprising the particles (930) into a rotatable vessel (200) through the top opening (210) of the rotatable vessel (200), such that the liquid is held by the lower portion (207) of the rotatable vessel (200), wherein the rotatable vessel (200) can comprise a longitudinal axis (201) about which the vessel (200) is rotatable, an upper portion (205) comprising a top opening (210) for receiving the liquid comprising the particles (930), a lower portion (207) for holding the liquid while the rotatable vessel (200) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (200) is rotating;

b) rotating the rotatable vessel (200) about its longitudinal axis (201) at a rotational speed, wherein the liquid comprising the particles (930) is moved to the lateral collection chamber (200) by centrifugal force, and wherein the centrifugal force is sufficient to sediment the particles (930) in the region of sedimentation (301) of the inner wall of the lateral collection chamber (220);

c) decelerating and ultimately stopping the rotation of the rotatable vessel (200), wherein the liquid flows back to the lower portion (207) of the rotatable vessel (200), wherein the angular deceleration is not sufficient to detach the particles (930) from the inner wall of the lateral collection chamber (220) by causing shearing forces between wall and liquid such that at least a part of the particles (930) remain attached to the inner wall of the lateral collection chamber (220), thereby separating at least said part of the particles (930) from the liquid;

d) withdrawing the liquid from the bottom of the rotatable vessel (200) while leaving the particles (930) in the lateral collection chamber (220);

e) adding the secondary liquid to the rotatable vessel (200) through its top opening (210);

f) rotating the rotatable vessel (200) about its longitudinal axis (201) in a first direction at a rotational speed; and g) decelerating and ultimately stopping the rotation of the rotatable vessel (200), wherein the angular acceleration in step f) and/or the angular deceleration in step g) is sufficient to detach at least a part of the particles (930) from the inner wall of the lateral collection chamber (220) by causing shearing forces between wall and liquid.

Steps f) and g) may be repeated one or more times in order to increase the efficiency of re-suspension.

The method described above can further comprise, in some embodiments, after step g):

h) rotating the rotatable vessel (200) about its longitudinal axis (201) in a second direction opposite to the first direction at a rotational speed, wherein the centrifugal force is not sufficient to sediment the particles (930) in the region of sedimentation (301) of the inner wall of the lateral collection chamber (220); and i) decelerating and ultimately stopping the rotation of the rotatable vessel (200), wherein the angular acceleration in step h) and/or the angular deceleration in step i) is sufficient to detach at least a part of the particles (930) from the inner wall of the lateral collection chamber (220) by causing shearing forces between wall and liquid.

As described before, steps f) and g), steps h) and i), and/or steps f) through i) may be repeated one or more times.

In some embodiments, in step f) and/or step h), the centrifugal force may not be sufficient to sediment the particles (930) in the region of sedimentation (301) of the inner wall of the lateral collection chamber (220).

Exemplary rates of acceleration and deceleration may be as follows:

The rate of deceleration in step c) may be from about 50 rpm/s to about 400 rpm/s or from about 50 rpm/s to about 1000 rpm/s.

The rate of acceleration in step f) and/or h) may be at least about 500 rpm/s, while the rate of deceleration in step g) and/or i) may be at least about 500 rpm/s.

In some embodiments of the method described herein, the relative amount of particles (930) remaining attached to the inner wall of the lateral collection chamber (220) at the end of step c) can be at least 50%, at least 80%, or at least 95%.

Also, in some embodiments of the method described herein, the relative amounts of particles (930) being detached from the inner wall of the lateral collection chamber (220) at the end of the re-suspension step(s) can be at least 50%, at least 80%, or at least 95%.

Also a method for mixing liquids by rotational movement is presented. The method can comprise:

a) introducing a liquid into a rotatable vessel (200) as described herein through the top opening (210) of the rotatable vessel (200), such that the liquid is held by the lower portion (207) of the rotatable vessel (200);

b) introducing a second liquid into the rotatable vessel (200) through the top opening (210) of the rotatable vessel (200), such that the liquid is held by the lower portion (207) of the rotatable vessel (200);

c) rotating the rotatable vessel (200) about its longitudinal axis (201) in a first direction;

d) decelerating and ultimately stopping the rotation of the rotatable vessel (200);

e) rotating the rotatable vessel (200) about its longitudinal axis (201) in a second direction opposite to the first direction; and f) decelerating and ultimately stopping the rotation of the rotatable vessel (200).

As described above, steps c) and d), steps e) and f), and/or steps c) through f) may be repeated one or more times if required to increase the effect of mixing.

As discussed herein, the rotatable vessel (200) described herein may be used in methods for isolation of biological target molecules involving analyte binding particles. For example, nucleic acids, proteins, or the like in a liquid biological sample (920) may be bound to analyte binding particles (930) and isolated from the surrounding liquid in a rotatable vessel (200) described herein.

Hence, a method for isolating an analyte that may be present in a liquid biological sample (920) is presented. The method can comprise:

a) introducing the liquid biological sample (920) into a rotatable vessel (200) through the top opening (210) of the rotatable vessel (200), such that the liquid is held by the lower portion (207) of the rotatable vessel (200), wherein the rotatable vessel (200) can comprise a longitudinal axis (201) about which the vessel (200) is rotatable, an upper portion (205) comprising a top opening (210) for receiving the liquid comprising the particles (930), a lower portion (207) for holding the liquid while the rotatable vessel (200) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (200) is rotating;

b) introducing analyte binding particles (930) into the rotatable vessel (200) through the top opening (210) of the rotatable vessel (200);

c) mixing the liquid biological sample (920) with the introduced analyte binding particles (930);

d) incubating the liquid biological sample (920) with the analyte binding particles (930) and thus binding the analyte to the analyte binding particles (930);

e) rotating the rotatable vessel (200) about its longitudinal axis (201) at a rotational speed, wherein the liquid comprising the analyte binding particles (930) is moved to the lateral collection chamber (200) by centrifugal force, and wherein the centrifugal force is sufficient to sediment the analyte binding particles (930) in the region of sedimentation (301) of the inner wall of the lateral collection chamber (220);

f) decelerating and ultimately stopping the rotation of the rotatable vessel (200), wherein the liquid flows back to the lower portion (207) of the rotatable vessel (200), wherein the angular deceleration is not sufficient to detach the particles (930) from the inner wall of the lateral collection chamber (220) by causing shearing forces between wall and liquid such that at least a part of the analyte binding particles (930) remain attached to the region of sedimentation (301) of the inner wall of the lateral collection chamber (220), thereby separating at least said part of the analyte binding particles (930) from the liquid;

g) withdrawing the liquid from the bottom of the rotatable vessel (200) while leaving the particles (930) in the lateral collection chamber (220);

h) adding the secondary liquid to the rotatable vessel (200) through its top opening (210);

i) rotating the rotatable vessel (200) about its longitudinal axis (201) in a first direction at a rotational speed; and j) decelerating and ultimately stopping the rotation of the rotatable vessel (200), wherein the angular acceleration in step i) and/or the angular deceleration in step j) is sufficient to detach at least a part of the particles (930) from the inner wall of the lateral collection chamber (220) by causing shearing forces between wall and liquid.

The method described above in some embodiments can further comprises after step j):

k) rotating the rotatable vessel (200) about its longitudinal axis (201) in a second direction opposite to the first direction; and l) decelerating and ultimately stopping the rotation of the rotatable vessel (200), wherein the angular acceleration in step k) and/or the angular deceleration in step l) is sufficient to detach at least a part of the particles (930) from the inner wall of the lateral collection chamber (220) by causing shearing forces between wall and liquid.

In some embodiments, during step i) and/or step k), the centrifugal force may not be sufficient to sediment the particles (930) in the region of sedimentation (301) of the inner wall of the lateral collection chamber (220)

Figure 7:
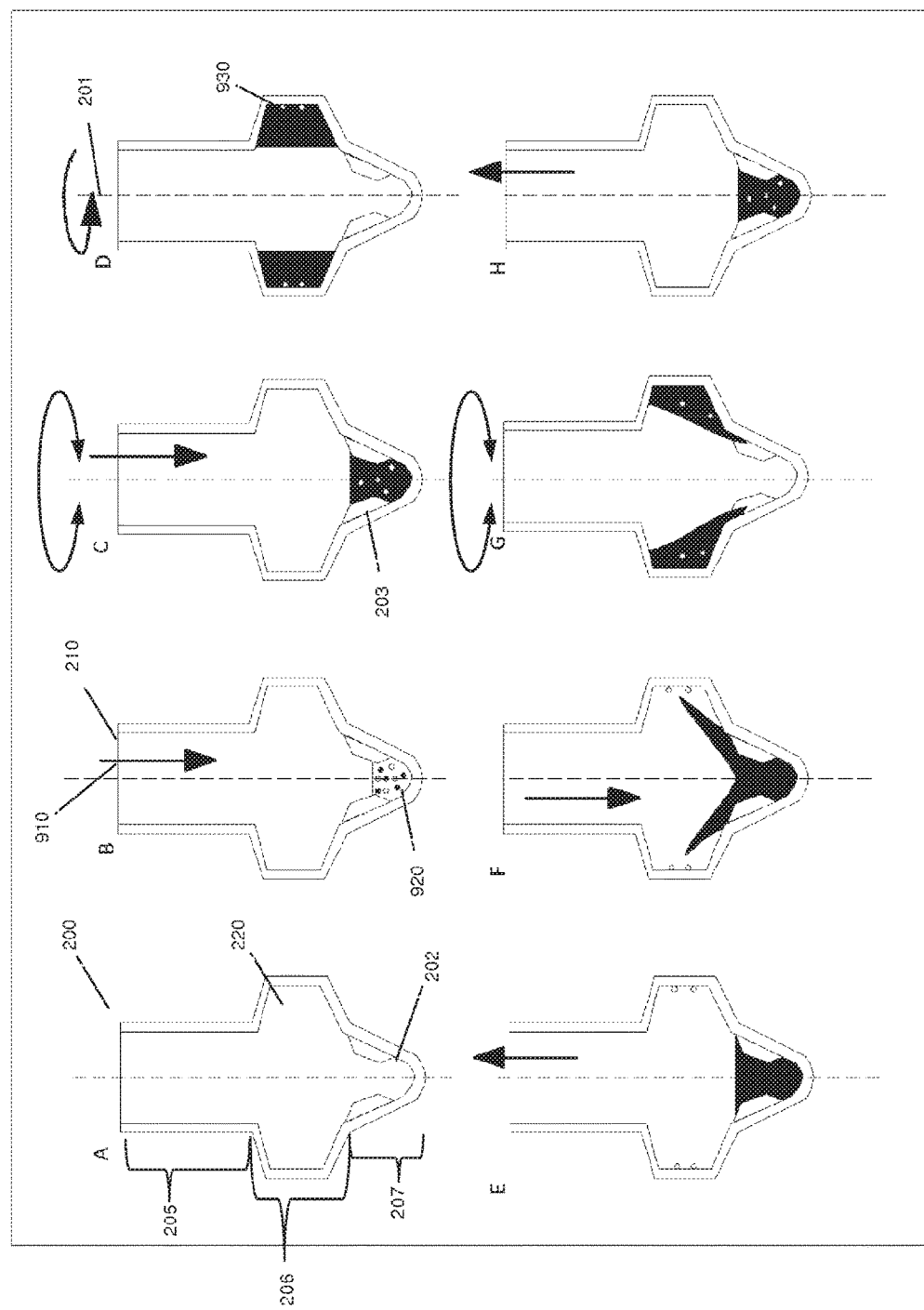
FIG. 7 illustrates a schematic overview of a workflow using the rotatable vessel described herein according to an embodiment of the present disclosure.

FIG. 7 schematically depicts a workflow for separating and suspending particles (930), wherein the part of the method for separating particles (930) is represented by steps A-E, and the part of the method for suspending particles (930) by steps F-H of FIG. 6.

An empty rotatable vessel (200) as described herein is depicted under A. As described above, it can have an upper portion (205), an intermediate portion (206) having a lateral collection chamber (220) and a lower portion (207) with an inner space (202) for holding a liquid biological sample (920).

A liquid biological sample (920) containing particles (930) can be introduced into the rotatable vessel (200) through its top opening (210) of the upper portion (205) as depicted as step B. The pipettor (910) carrying out the dispensing of the liquid biological sample (920) is represented by the arrow.

In step C, a reagent can be added, such as a lysis buffer, a binding buffer, a staining reagent, or the like. In order to mix the components, the rotatable vessel (200) can be rotated about its longitudinal axis (201) at a relatively low rotational speed. The rotation of the rotatable vessel (200) can induce a rotational flow of the liquid biological sample (920) containing particles (930). This induction can be facilitated by the baffles (203) protruding from the inner wall of the lower portion (207) of the rotatable vessel (200). The rotational movement can, in some embodiments, be periodically applied in one or in both directions. In some embodiments, the acceleration and/or deceleration can be performed gradually, thus avoiding undesired effects such as spilling of the liquid biological sample (920) through the top opening (210), or causing bubbles, or the like.

In the following step (D), a separation step, the rotatable vessel (200) can be rotated at a higher rotational speed than before, in one direction only, for a predefined period of time. In some embodiments while executing the separation step, the liquid present in the lateral collection chamber (220) can be exposed to a relative centrifugal force (rcf) in a range of about 10 to about 10000 g. In the case of the separation of blood cells such as WBCs, the rcf can be, in some embodiments, in a range of about 50 to about 2000 g, in further embodiments in a range of about 200 to about 1000 g, and the separation time can be in some embodiments in a range of about 5 to about 500 s, in further embodiments in a range of about 20 to about 120 s. The skilled person is able to select the parameters for executing the separation step based on the laws of sedimentation This higher speed can be sufficient for the liquid biological sample (920) including the particles (930) to be pressed into the lateral collection chamber (220). The particles (930) can sediment in the region of sedimentation (301) on the surface of the inner wall of the lateral collection chamber (220) and can remain there after the rotational movement has stopped, while the liquid can flow back into the inner space (202) of the lower portion (207) of the rotatable vessel (200) under the force of gravity. In order to not release particles back to the liquid while stopping, the deceleration can take place under controlled conditions. The critical value of deceleration can generally be adapted to each case and can often be experimentally evaluated and depend on parameters such as the type of particles (930), adhesion force of the particles (930) to the wall of the lateral collection chamber (220), exposure of the particles (930) to flow induced by stopping, geometric aspects of the rotatable device (200) such as the presence and geometry of vertical grooves (302), viscosity of liquid, amount of liquid present in the device, initial rotation speed, or other parameters. In some embodiments, the speed of deceleration for processed blood cells can be in a range of about 50 to about 1000 rpm/s, in further embodiments in a range of about 50 to about 400 rpm/s. Also, deceleration may be conducted in two or more phases. Suitable structures for executing the deceleration in a controlled manner can include in some embodiments electromotors with corresponding motion controllers.

The liquid biological sample (920) deprived of at least a part of the particles (930) can then, in step E, be withdrawn by the pipettor (910) without disturbing the sedimented particles (930).

A different liquid such as a wash buffer, re-suspension buffer or other reagent can be dispensed into the rotatable vessel (200) through its top opening (210) by the pipettor (910) in step F.

Steps F and G can feature re-suspension of the separated particles (930) in an initially particle-free secondary liquid. For re-suspension, a corresponding profile can be used involving alternating and/or repeated phases of rotational acceleration and/or deceleration. Re-suspension can be achieved through a sufficient velocity difference between the wall of the lateral collection chamber (220) and the liquid in the lateral collection chamber (220), without generating unnecessary high shearing forces which may cause disruption of sensitive particles (930) or without causing high and long-lasting centrifugal forces. These velocity differences can contribute to overcoming the adhesion forces between the particles (930) and the wall of the lateral collection chamber (220). In some embodiments, speeds of acceleration and deceleration for processed blood cells can be >500 rpm/s.

More generally, in some embodiments the rate of deceleration in step c) can be smaller than any of the rates of acceleration or deceleration in steps f) or g).

The re-suspended particles can, in step H, be retrieved with the pipettor (910) and may be used for downstream processing such as, for example, analytic methods.

The method described above can make use of the inertia of the centrifuged liquid in an ingenious way. When decelerating the rotatable vessel (200) during the separating step, the pseudo force caused by the rotating liquid can be reduced by keeping the rate of deceleration at a relatively low level so as to not disturb the particles (930) sedimented at the inner wall of the lateral collection chamber (220).

In the re-suspension step(s), on the other hand, the inertia of the liquid can be used to the opposite end by facilitating the detachment of the sedimented particles (930) via sufficiently high rates of angular acceleration and or deceleration, as described above.

The methods described herein are widely applicable especially, although not only, in the field of diagnostics, particularly analysis of clinical sample material.

In some embodiments, the liquid biological sample (920) can be a human sample, such as blood, including whole blood, blood plasma or serum, saliva, ocular lens fluid, cerebrospinal fluid, sweat, urine, stool, semen, milk, ascites fluid, mucous, synovial fluid, peritoneal fluid, amniotic fluid, tissue, cultured cells, or the like.

In some embodiments, tissue can be prepared as to yield a suspension containing the cells to be processed. Suitable protocols for preparing tissue samples are known to the skilled person.

In other embodiments, the liquid biological sample (920) is human blood or derived therefrom, such as whole blood, plasma, or serum. As known to the skilled artisan, whole blood obtained from a subject may be prepared in various manners. In the case of whole blood, for example, the sample may be diluted with anticoagulants such as heparin, citrate, chelating agents such as EDTA, EGTA, or other anticoagulants. Particles of interest in a blood sample are, in some embodiments, pathogens such as viruses like HIV, HBV, HCV, CMV, WNV, SLEV, JEV, HSV, influenza, or other viruses. Other pathogens potentially present in human blood may be bacteria, such as the genera *Neisseria, Chlamydia, Mycobacterium, Yersinia, Borrelia, Proteus, Enterococcus, Staphylococcus* such as methicillin-resistant or-sensitive *Staphylococcus aureus, Meningococcus, Escherichia, Clostridium*, or other bacteria. Also, fungi may be pathogenic particles of interest present in human blood, for example, the genera *Candida, Aspergillus, Saccharomyces*, or other fungi.

In other embodiments, human cells can be particles of interest in human blood, such as blood cells, including white blood cells (WBC) such as monocytes, granulocytes (basophilic, eosinophilic, or neutrophilic ones), macrophages, T-lymphocytes or B-lymphocytes, plasma cells, or lymphatic or myeloic stem cells, thrombocytes, erythrocytes, circulating tumor cells, a mixture of different blood cells and/or tumor cells, or other blood cells.

In some embodiments, human cells can be processed for hematologic analyses, such as three-part-differential or five-part differential analyses. Also in some embodiments, the human cells can be processed to be subsequently subjected to flow cytometric analysis.

In such embodiments, the processing may comprise labeling of the cells with, for example, antibodies directed to specific cell surface antigens. In some embodiments, the particles can be human white blood cells (WBCs). The processing may then include labeling of the WBCs using, for example, labeled antibodies specific for the surface antigens CD2/CD3 for T cells, CD14 for monocytes, CD15 for granulocytes and monocytes, CD16 for macrophages, CD36 for platelets, monocytes and macrophages, CD45 for leucocytes. As described above, such antibodies or other binding molecules may also be present as retention structures in the region of sedimentation (301) on the surface of the inner wall of the lateral collection chamber (220) of the rotatable vessel (200) described herein.

After labeling the blood cells of interest with antibodies that may include labels, such as fluorescent or electroluminescent labels, the cells may be readily identified, for example, in the flow cell of a flow cytometer. A variety of embodiments may be appropriate to deliver the processed cells from the rotatable vessel (200) to the flow cytometer or other analytical module. For instance, the re-suspended processed particles may be withdrawn from the rotatable vessel (200) with a pipettor (910) and then dispensed into an inlet of the flow cytometer. The processing station (100) and the flow cytometer or other analytic module may, in some embodiments, be surrounded by a mutual housing.

Methods for Processing Particles Using Specific Embodiments of the Rotatable Vessel A Method for Separating Particles of Various Sedimentation Speeds The method of this embodiment can include applying a velocity program allowing the discrimination of particles (930) of various sedimentation speeds, being adapted to force the particles (930) of faster sedimentation speed to mainly sediment, while the particles (930) with slower sedimentation speed remain mainly in suspension. The difference in speed of sedimentation may in some embodiments be influenced by the density of the suspending media (for example, by using a CsI, CsCl, sucrose or other density gradient material such as Histodenz®, Nycodenz®, Optiprep®, or the like). The speed of sedimentation can otherwise mainly be defined by the density of the particle (930), the density and viscosity of the surrounding liquid and the diameter of the particle (930) and by the applied centrifugal force.

In some embodiments, the steps of a method of such an embodiment can be as follows:

a) applying a suspension of particles (930) of two classes to a rotatable vessel (300) of an embodiment as shown in FIGS. 3A-D. The particles (930) of the first class have a higher speed of sedimentation than the particles (930) of the second class;

b) carrying out steps A-D of the method depicted in FIG. 6;

c) removing the supernatant which mainly contains the particles (930) with the slower sedimentation speed, while the particles (930) with the faster sedimentation speed are mainly retained in the region of sedimentation (301); and d) in some embodiments, adding a second liquid such as a resuspension buffer or reagent to the rotatable vessel (300) and resuspending the particles (930) remaining in the rotatable vessel (300) by applying the method of resuspension as shown in steps F-H of FIG. 6. In some embodiments, step d) further comprises adding a buffer having a higher density than the separated particles (930) in order to release the particles (930).

A Method for carrying out a Reaction in a Rotatable Vessel

In this embodiment, temperature and/or time of incubation can be controlled within the rotatable vessel (200) containing educts of a reaction, such as blood cells and antibodies as described above, in order to sufficiently complete a reaction, in some embodiments including occasional or continuous application of controlled bi-directional rotation (as described in the context of step C or G of FIG. 6) in order to keep the particles (930) in suspension.

Methods for Processing Particles using a Rotatable Vessel having a Burst Valve

In some embodiments, the method depicted in FIG. 6 can be performed with a rotatable vessel (400) having a burst valve (450). In such embodiments, the method for separating particles (930) from a liquid biological sample (920) can comprise:

a) introducing the liquid biological sample (920) comprising the particles (930) into a rotatable vessel (400)

through the top opening (210) of the rotatable vessel (400), such that the liquid is held by the lower portion (207) of the rotatable vessel (400), wherein the rotatable vessel (400) comprises a longitudinal axis (201) about which the vessel (400) is rotatable, an upper portion (205) comprising a top opening (210) for receiving the liquid comprising the particles (930), a lower portion (207) for holding the liquid while the rotatable vessel (400) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (400) is rotating;

b) rotating the rotatable vessel (400) about its longitudinal axis (201) at a first rotational speed, wherein the centrifugal force is sufficient to sediment the particles (930) in the region of sedimentation (401) of the lateral collection chamber (220), while the surrounding liquid is also pressed into the collection chamber (220), and wherein the hydrostatic pressure caused by the centrifugal force does not exceed the critical value of the burst valve (450), such that the burst valve (450) remains liquid-tight; and c) rotating the rotatable vessel (400) about its longitudinal axis (201) at a second rotational speed higher than the first one, wherein the hydrostatic pressure caused by the centrifugal force exceeds the critical value of the burst valve (450) such that the liquid is pressed through the burst valve (450) out of the rotatable vessel (400), while at least a part of the particles (930) remains in the lateral collection chamber (220).

In an embodiment including a rotatable vessel (400) having a burst valve (450), the method for suspending particles (930) in a liquid can comprises:

a) rotating a rotatable vessel (400) as described herein containing the particles (930) in a liquid about its longitudinal axis (201) in a first direction at a rotational speed, wherein the hydrostatic pressure caused by the centrifugal force does not exceed the critical value of the burst valve (450), such that the burst valve (450) remains liquid-tight, wherein the rotatable vessel (400) comprises a longitudinal axis (201) about which the vessel (400) is rotatable, an upper portion (205) comprising a top opening (210) for receiving the liquid comprising the particles (930), a lower portion (207) for holding the liquid while the rotatable vessel (400) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (400) is rotating;

b) decelerating and ultimately stopping the rotation of the rotatable vessel (400)

c) rotating the rotatable vessel (400) containing the particles (930) in a liquid about its longitudinal axis in a second direction opposite to the first direction at a rotational speed, wherein the hydrostatic pressure caused by the centrifugal force does not exceed the critical value of the burst valve (450), such that the burst valve (450) remains liquid-tight.

In some embodiments, the above-described method further comprises step c):

d) rotating the rotatable vessel (400) about its longitudinal axis (201) at a second rotational speed higher than the previous ones, wherein the hydrostatic pressure caused by the centrifugal force exceeds the critical value of the burst valve (450) such that the liquid is pressed through the burst valve (450) out of the rotatable vessel (400), while at least a part of the particles (930) remains in the lateral collection chamber (220).

Methods for Processing Particles using a Rotatable Vessel having a Peripheral Filter In some embodiments, the method depicted in FIG. 6 can be performed with a rotatable vessel (500) having a peripheral filter (550). In such embodiments, the method for separating particles (930) from a liquid biological sample (920) can comprise:

a) introducing the liquid biological sample (920) comprising the particles (930) into a rotatable vessel (500) as described herein through the top opening (210) of the rotatable vessel (500), such that the liquid is held by the lower portion (207) of the rotatable vessel (500), wherein the lateral collection chamber (220) of the intermediate portion (206) of the rotatable vessel (500) comprises a peripheral filter (550) and wherein the rotatable vessel (500) comprises a longitudinal axis (201) about which the vessel (500) is rotatable, an upper portion (205) comprising a top opening (210) for receiving the liquid comprising the particles (930), a lower portion (207) for holding the liquid while the rotatable vessel (500) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (500) is rotating; and b) rotating the rotatable vessel (500) about its longitudinal axis (201) at a rotational speed, wherein the centrifugal force is sufficient to sediment the particles (930) in the region of sedimentation (301) of the lateral collection chamber (220), while the liquid is pressed through the peripheral filter (550) out of the rotatable vessel (500).

In such embodiments, the separation of non- or poorly compressible material such as artificial beads made of glass or hard plastics can be advantageously carried out, since such particles (930) can be less prone to clogging the pores of the peripheral filter (550) than significantly deformable particles (930). For the latter, the following embodiment may be more advantageous.

In that embodiment, the method for separating particles (930) from a liquid biological sample (920) can comprise:

a) introducing the liquid biological sample (920) comprising the particles (930) into a rotatable vessel (500) through the top opening (210) of the rotatable vessel (500), such that the liquid is held by the lower portion (207) of the rotatable vessel (500), wherein the lateral collection chamber (220) of the intermediate portion (206) of the rotatable vessel (500) comprises a peripheral filter (550) and wherein the rotatable vessel (500) can comprise a longitudinal axis (201) about which the vessel (500) is rotatable, an upper portion (205) comprising a top opening (210) for receiving the liquid comprising the particles (930), a lower portion (207) for holding the liquid while the rotatable vessel (500) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (500) is rotating; and b) rotating the rotatable vessel (500) about its longitudinal axis (201) at a rotational speed with dedicated phases of acceleration and/or deceleration and thus centrifugal speed, wherein the liquid flow in the lateral collection chamber (220) has a radial component and a tangential component of speed, causing cross-flow filtration to occur, such that the resulting combination of radial force and tangential force acting on the particles (930) prevent the particles (930) from sedimenting in the region of sedimentation (301) of the lateral collection chamber (220), while the liquid is pressed through the peripheral filter (550) out of the rotatable vessel (500).

In this embodiment employing cross-flow filtration, the tangential vector component can counteract the sedimentation of the particles (930) on the inner wall of the collection chamber (220). In brief, the dedicated phases of acceleration and/or deceleration can lead to a movement of the particles (930) tangential/parallel to the surface of the inner wall of the lateral collection chamber (220), based on the inertia of the particles (930) in movement. For instance, when the rotatable vessel (500) is decelerated, the liquid and thus the particles (930) within can, due to the inertia of masses in movement, temporarily rotate quicker about the rotational axis (201) than the rotatable vessel (500) on which the decelerating force is directly applied. Analogously, during acceleration, the vessel (500) can temporarily rotate quicker than the liquid and thus the particles (930).

In some embodiments, the peripheral filter (550) of the rotatable vessel (500) can have a burst function as described for the embodiment of the rotatable vessel (400) having a burst valve (450).

In an embodiment including a rotatable vessel (500) having a burst valve (550), the method for suspending particles (930) in a liquid can comprise:

rotating a rotatable vessel (500) as described herein containing the particles (930) in a liquid about its longitudinal axis (201) in a first direction at a rotational speed, wherein the hydrostatic pressure caused by the centrifugal force is not sufficient to press the liquid through the peripheral filter (550) out of the rotatable vessel (500) and wherein the rotatable vessel (500) can comprise a longitudinal axis (201) about which the vessel (500) is rotatable, an upper portion (205) comprising a top opening (210) for receiving the liquid comprising the particles (930), a lower portion (207) for holding the liquid while the rotatable vessel (500) is resting, the lower portion (207) comprising a bottom, and an intermediate portion (206) located between the upper portion (205) and the lower portion (207), the intermediate portion (206) comprising a lateral collection chamber (220) for holding the liquid while the rotatable vessel (500) is rotating;

decelerating and ultimately stopping the rotation of the rotatable vessel (500); and rotating the rotatable vessel (500) containing the particles (930) in a liquid about its longitudinal axis (201) in a second direction opposite to the first direction at a rotational speed, wherein the hydrostatic pressure caused by the centrifugal force is not sufficient to press the liquid through the peripheral filter (550) out of the rotatable vessel (500).

FIG. 8 displays an imaging method for particles (930) using a rotatable vessel (700) having an annular peripheral wall. Each of the steps A, B, C and D is shown in a side view of a vertical cross-section in the upper part of the figure, and a top view of a horizontal cross-section in the lower part of the figure.

While the empty rotatable vessel (700) is shown in step A, the depiction of step B illustrates the vessel (700) filled with a suspension of particles (930) such as biological cells or viruses which are centrifuged in step C by rotating the vessel (700) about its longitudinal axis (201) in the direction of the curved arrow. The straight arrows indicate the direction of the centrifugal forces applied to the particles (930). In step D, the vessel (700) is resting again, with the centrifuged particles (930) attached to the axis-far wall (712) of the annular peripheral chamber (710). The vessel may now be optically analyzed, for example in an arrangement as shown in FIG. 1C.

Therefore, a method for optically analyzing particles (930) contained in a liquid biological sample (920) can comprise:

introducing the liquid biological sample (920) comprising the particles (930) into a rotatable vessel (700) with an annular peripheral chamber (710) through a top opening (210) of the rotatable vessel (700) into the annular peripheral chamber (710), wherein the rotatable vessel (700) can comprise a longitudinal axis (201) about which the vessel (700) is rotatable, a transparent outer wall (712), an upper portion (205) comprising a top opening (210) for receiving the liquid biological sample (920) comprising the particles (930), and an intermediate portion (206) located below the upper portion (205), the intermediate portion (206) comprising an annular peripheral chamber (710) for holding the liquid, the annular peripheral chamber (710) comprising on the surface of its inner wall a region of sedimentation (301) for the particles (930) contained in the liquid biological sample (920), wherein the annular peripheral chamber (710) is fluidically connected to the top opening (210);

rotating the rotatable vessel (700) about its longitudinal axis (201) at a rotational speed, wherein the centrifugal force is sufficient to sediment the particles (930) in the region of sedimentation (301) of the annular peripheral chamber (710); and optically analyzing the particles (930) with a scanner (600) comprising imaging optics (640).

The embodiments described herein for the methods using rotatable vessels not having an annular peripheral chamber can also be applicable to the method using a rotatable vessel (700) having an annular peripheral chamber.

In the context of processing the results of optical analysis, it may be advantageous to exploit both statistical data—obtainable through analyzing a sufficiently large number of cells—and morphological data especially in cases where the particles (930) are biological cells.

The correlation between statistical data and morphological data can usually require a considerable amount of experience of the person in charge of data interpretation. Morphology can usually be examined by microscopy, often without immunostaining at all and/or without generating statistical data such as absolute or relative occurrence. The morphology of rare (and thus rarely occurring) cells can often not be identified at all.

Statistical data on cell populations (such as the absolute or relative occurrences of dedicated cells) can often be acquired by Fluorescence-Associated Cell Sorting (FACS) without yielding much information on morphology. The frequently used forward and side-scatter analysis can only provide limited and rather general morphologic data.

When using a flow cytometer, statistical data from cell analysis can be arranged as a table wherein each cell is represented in a row, often displaying a forward scatter, a sideward scatter and a number of fluorescence values. Each fluorescent signal may represent a specific property of the analyzed cell, for example, the expression of a CD-marker. Such data can mostly be numerical and hence do not include detailed morphological information on the cells.

Based on these data, grouping of cells can be done by setting conditions for the different values mentioned above. Various ranges may be combined in order to select a distinct group of cells within the total number of cells analyzed. For instance, T4-helper cells may be selected based by a positivity of cells for a CD4 marker. The result of such a grouping can be a statistics, typically listing the absolute or the relative concentration of certain types of cells having certain characteristics. Other statistics may focus on the range of expression of a certain marker.

A typical analysis may list the values of 100,000 cells per analysis, allowing a good precision also for rarely occurring cells. For example, a subpopulation with 1 k/100 kcells can still be analyzed with a precision of 3.2% VK, a population of 100 cells/100 kcells with a precision of 10% VK.

In certain applications, such as MRD (minimal residual disease), even a larger total number of cells may be analyzed, for example, 1×10E6 cells/analysis, and the number of cells searched (of "residual" cells") can be between about 10 and about 100 cells. For such a large number of cells the data acquisition effort and data produced and the data processing time can be large.

The statistical data taken alone can display a number of limitations: Firstly, in order to interpret the data, which can require a correct classification of cells, a large amount of experience and/or controls or reference analyses can be required, as the classification can solely be based on numerical values. Secondly, complex data potentially including data from unexpected cells can be difficult to interpret. Such unexpected cells may appear often in samples taken from patients suffering from certain diseases. Thirdly, the statistical data alone can be misleading, for example in the case of cells adhering to each other. Such cells may be regarded as one double positive single cell. Further, the absence of any morphologic data may not provide any information of the subcellular origin (such as an organelle, the plasma membrane, or the like) of the measured signal. The absence of morphologic information can make it difficult to exclude artefacts such as doublets, cell-clusters and debris.

Morphological data, on the other hand, can often be obtained by microscopy (bright-field or fluorescence microscopy, in some cases involving a digital camera). The morphological data, especially if combined with specific stains, can allow detecting and/or confirming certain diseases.

Again, morphological data taken alone can be subject to a number of limitations: Generally the number of cells which can be inspected from one patient by this method, if not automated, can be low, due to the time to acquire the data and inspect the data. Also, the to time to find a distinct cell of a distinct class within a large number of cells can be very time consuming, especially when the respective cells are rare. Moreover, the correlation with statistical data may not be given. When examining a specific cell, it may not be clear what its relative or absolute concentration in the sample is. Finally, the interpretation of expression levels of a distinct CD-marker or the like would require comparison to a control or a reference sample.

In the context of the methods, devices and systems described herein, it is an aspect to generate, measure and/or report from one patient:

a) a statistical data set related to at least one cell population, such as an absolute or relative occurrence of a cell type, or an expression level, and b) a morphological data set, such as set of bright-field, reflectance, absorbance and/or fluorescence images.

In such embodiments, the automatically produced and combined data can allow for better data interpretation, better patient to patient comparison, better monitoring of one patient over time and better comparison among sites. In summary, the certainty can be increased that the cells counted/reported belong to the respective target class.

In order to reduce data acquisition time and/or the amount of data, the statistical data may be acquired at a lower geometric resolution, allowing a higher rate of cells analyzed per time. The morphological data, on the other hand, may be generated at a higher geometric resolution, and only from a limited number of cells.

The employed analytical system may be adjusted depending on which types of cells are to be imaged (in morphological quality) and the number of cells to image. The criteria may be defined such that the system acquires the data autonomously.

Among the advantages of the above-described approach using both morphological and statistical data can be the following:

It can be verified by cross-checking between statistical and morphological data whether the counted cells are in fact the target cells to be analyzed, thus leading to improved data conformity and more reliable results.

Unusual data can be interpreted in a more detailed and reliable manner, thus facilitating diagnosis of sickness.

Artefacts can be identified and excluded from the results.

The amount of controls can be reduced.

The level of experience and expertise required from the user is considerably diminished.

EXAMPLES

The following experiments are intended to exemplify non-limiting embodiments of the automated system, the rotatable vessel and the methods described herein.

Example 1: Mixing Two Liquids in the Device

Objective:

Mix a liquid biological sample (920) containing particles (930) with a second liquid such as a wash buffer, diluent, reagent, lysis buffer, stabilizer for reagents, fixative for cells, dye, antibody solution, or the like. Such a method may be, for example, used for cell processing for flow cytometric analysis including washing, lysing, fixing, or staining cells.

Materials:

1. Rotatable vessel (300) according to FIG. 3B with a maximum inner diameter of the intermediate portion (206) of 28 mm. The volume within the vertical grooves (302) was 100 μl. The volume of the lateral collection chamber (220) and the inner space (202) of the lower portion (207) were each approximately 1.2 ml, allowing a maximum processing volume of about 1 ml. The rotatable vessel (300) was made of PMMA. For production of the rotatable vessel (300) used in this experiment, two separate parts had been drilled and joined together.

2. Sample processing station (100) having a 50 W-DC motor, with a Hall sensor, from the company Maxon, having a 500 pulse/rotation encoder. The motor was controlled by a dedicated controller (Maxon EPOS2). The controller itself received its instructions from software controlling elements of movement, such as values for acceleration, maximal speed, time at maximal speed, deceleration profiles and/or rotation profiles versus time. The rotary actuator (101) was mounted to a console (103). The rotatable vessels (300) were attached to the axis of the rotary actuator (101) and secured.

Processing Parameters:
1. Mixing protocol:
    M1: With an acceleration of 1800 RPM/sec to a final speed of 3600 RPM, in a clockwise direction, then with a deceleration of 1800 RPM/sec to a final speed of 0 RPM. This motion equals 120 rotations in a clockwise direction.
    M2: With an acceleration of 1800 RPM/sec to a final speed of 3600 RPM, in a counter-clockwise direction, then with a deceleration of 1800 RPM/sec to a final speed of 0 RPM. This equals 3960°=120 rotations in a counter-clockwise direction.
Repeat 5 times (M1→M2)
Experiment Conducted:
1. The rotatable vessel (300) was mounted to a processing station (100)
2. 150 µl of whole blood were pipetted into the rotatable vessel (300) through its top opening (210) to settle at the bottom of the inner space (202) of the lower portion (207) of the rotatable vessel (300).
3. 800 µl of PBS buffer (GIBCO, Life technologies, No 10010-15) were added to the whole blood in the rotatable vessel (300).
4. The blood and the PBS were mixed by applying a mixing protocol using an oscillating forward and backward spinning according to step C or G of the method shown in FIG. 6.

Observations:
By execution of the mixing protocol (a movement applied to the rotatable vessel (300) according to the processing parameters mentioned above), the liquids were moved by the applied rotational acceleration exerted via the rotary actuator (101), whereby the baffles (203) contributed to moving the liquid, resulting in moving the two liquids into the lateral collection chamber (220). Upon deceleration, the combined liquids moved partially down to the inner space (202) of the lower portion (207). By repetition of this movement, the two liquids are thoroughly mixed due to the periodic forward and backward rotary motion.

Measurements with a hematology analyzer confirmed the homogeneity of the mix and the integrity of the cells.

Example 2: Isolation of Blood Cells

Objective:
In certain blood sample preparation protocols for flow cytometry, it is required to remove the blood cells from the surrounding plasma.
Material:
1. Rotatable vessel (300): as in Example 1
2. Processing station (100): as in Example 1
Processing Parameters:
Separation Protocol:
    S1: Accelerate with 2000 RPM/sec from 0 RPM to a final speed of 8000 RPM (Revolutions per Minute)
    S2: Hold speed at 8000 RPM for 30 sec
    S3: Decelerate from 8000 RPM to 1000 RPM, with a deceleration of 250 RPM/sec
    S4: Decelerate from 1000 RPM to 0 RPM with a deceleration of 50 RPM/sec
Experiment Conducted:
1. The rotatable vessel (300) was mounted to a processing station (100)
2. 150 µl of blood were mixed with 800 µl of PBS buffer according to Example 1
3. A separation protocol was applied as mentioned above (Example 2)
4. The cell-free liquid was removed from the interior of the rotatable vessel (300), while the cells (930) remained in the lateral collection chamber (220). For removal of the cell-free liquid a pipette with a disposable tip was used.

Observations:
During the separation phase of this protocol (during 30 sec at 8000 RPM), the fluid biological sample (920) moves to the lateral collection chamber (220), forming a ring-like volume around the longitudinal spin axis (201). Under the influence of centrifugal force (at 8000 RPM) and at a radius of 14 mm, the relative radial acceleration is approximately 1000 g (=1000× gravity of earth), the cells (930) of a higher relative density (red and white blood cells) moved to the region of sedimentation (301). Visual inspection through the—in this embodiment—transparent rotatable vessel (300) indicated that the cells (930) moved within approximately 5 seconds to the outer wall.

After the separation of the target particles (blood cells, 930) was completed (30 sec), the stopping phase was initiated. During this phase, the rotational speed of the rotatable vessel (300) was gradually decreased in a controlled manner down to 0 RPM. The deceleration was conducted in two steps: from 8000 to 1000 RPM with 250 RPM/sec and from 1000 RPM to 0 RMP with 50 RPM/sec.

The previously established deceleration program was sufficiently mild to not re-suspend the separated particles. When during deceleration the relative radial acceleration decreased to approximately <1 g (at 300 RPM), the cell-free liquid moved down from the lateral collection chamber (220) (220) to the inner space (202) of the lower portion (207), while the blood cells (930) remained in the lateral collection chamber (220).

Once the rotation of the rotatable vessel (300) stopped, the particle-free solution (mixture of PBS and serum or plasma from the blood) was removed from the rotatable vessel (300) by aspirating the liquid from the bottom of the lower portion (207) using a pipette with a disposable tip, while the blood cells remained in the vertical grooves (302) of the lateral collection chamber (220), available for further processing such as re-suspension.

Measurements with a hematology analyzer confirmed that the removed supernatant was virtually cell-free.

Example 3: Release and Resuspension of Separated Cells from the Lateral Collection Chamber Objective:
The release and resuspension of cells (930) adhering to the inner surface of the lateral collection chamber (220) or retained in the vertical grooves (302) of the lateral collection chamber (220). The cells (930) had been processed beforehand according to Example 2.

Purpose of such a cell release and cell resuspension is to ready the cells (930) for further processing, for example, for fixing, lysing, staining and/or washing the cells (930) or parts of the cells (930). Another purpose is to collect the cells (930) for other desirable purposes such as cultivation. The resuspended cells (930) may be removed from the device by using a pipettor (920).
Material:
1. Rotatable vessel (300): as in Example 1
2. Processing station (100): as in Example 1
Processing Parameters:
Resuspension Protocol:
R1: With an acceleration of 4800 RPM/sec to a final speed of 4800 RPM, in a clockwise direction, hold 0.5 sec at final speed, then with a deceleration of 9'600 RPM/sec to a final speed of 0 RPM. This equals 100 rotations in a clockwise direction, wait 1 sec.

R2: With an acceleration of 4800 RPM/sec during 1980° (=5.5 full turns) to a final speed of 4800 RPM, in a counter-clockwise direction, hold 0.5 sec at final speed, then with a deceleration of 9600 RPM/sec to a final speed of 0 RPM. This equals 100 rotations in a counter-clockwise direction, wait 1 sec Repeat 5 times (R1→R2)

Experiment Conducted:
1. Cells (930) from 150 µl blood were separated and retained by the vertical grooves (302) of the lateral collection chamber (220) according to Example 2.
2. A volume of 400 µl of PBS buffer (as "Cell release buffer" CRB) was added to the inside of the rotatable vessel (300) through its top opening (210).
3. The resuspension protocol described above was applied.

Observations:

By applying the resuspension protocol, 400 µl of CRB were moved to the lateral collection chamber (220). By means of the forward and backward acceleration and deceleration of the rotatable vessel (300), the cell release buffer was moved forward and backward in the lateral collection chamber (220). By this movement cells adhering to the region of sedimentation (301) of the inner surface of the wall of the lateral collection chamber (220) or retained in the vertical grooves (302) were released and resuspended in the CRB.

Measurements with a hematology analyzer showed a yield of resuspended cells (930) of >90% (erythrocytes & WBCs), and the integrity of the cells (930) was unaffected. The mass of the remaining liquid in the device was measured to be about 100 mg.

Example 4: Preparation of WBCs

Objective:
Production of washed white blood cells (WBCs) from whole blood: By mixing the whole blood with a lysis buffer for selective lysis of the red blood cells (RBCs), removal of the lysed RBCs from unlysed WBCs, and subsequent wash of the WBCs. Cells processed in this manner are, for instance, well suited for being stained with antibodies and/or for flow cytometry analysis.

Materials:
1. A rotatable vessel (300) according to FIG. 3A with a maximum inner diameter of the intermediate portion (206) of 28 mm. The volumes of the lateral collection chamber (220) and the inner space (202) of the lower portion (207) were each approximately 1.2 ml, allowing a maximum processing volume of about 1 ml. The rotatable vessel (300) was made of PMMA. For the production of the rotatable vessel (300) used in this experiment, two separate parts had been drilled and joined together.
2. Processing station (100): as in Example 1

Processing Parameters:
Mixing protocol: as in Example 1
Cell separation protocol: as in Example 2
Resuspension protocol: as in Example 3

Experiment Conducted:
1. A rotatable vessel (300) was mounted to a processing station (100)
2. 100 µl of whole blood were added into the rotatable vessel (300)
3. 800 µl of RBC lysis buffer (Biolegend®, No 420301, ammonium chloride, 1×) were added to the whole blood
4. A mixing protocol was executed
5. The mix was incubated for 20 minutes, in order to complete the lysis of the RBCs
6. A cell separation protocol was executed in order to separate the WBCs from the lysed RBCs
7. The liquid in the inner space (202) of the lower portion (207) and mainly lysed RBCs were removed (to waste)
8. 800 µl of PBS (Phosphate buffered saline, 1×) were added into the rotatable vessel (300) in order to wash the WBCs
9. A resuspension protocol was applied
10. A separation protocol was applied
11. The cell-free liquid was removed (to waste)
12. 400 µl PBS as cell release buffer were added to the rotatable vessel (300)
13. A resuspension protocol was applied
14. The liquid containing the WBCs, resuspended in the cell release buffer, was removed from the rotatable vessel (300) and subsequently analyzed.

Observations:
The recovery rate for WBCs was >90%, residual RBCs were in the range of <2%, liquid was removed to a residual amount of <4%. The residual mass in the rotatable vessel (300) was approximately 50 mg.

Example 5: Staining of WBCs

Objective:
Staining of WBCs with subsequent analysis, counting and classification in a flow cytometer.

Materials:
1. Rotatable vessel (300): as in Example 4
2. Processing station (100): as in Example 4

Processing Parameters:
Mixing protocol: as in Example 4
Cell separation protocol as in Example 4
Re-suspension protocol as in Example 4

Experiment Conducted:
1. WBCs were processed as in Example 4, except the cells were only re-suspended with 200 µl PBS-buffer.
2. 6.4 µl anti-human CD45-Antibody labeled with the fluorescent dye Allophycocyanin (Supplier: Biolegend) was pipetted to the cell suspension OR alternatively 2 µl Thiazole-orange (Supplier: Sigma Aldrich, 2 mg/ml in DMSO) were added.
3. A mixing protocol was applied.
4. The cells were incubated at ambient temperature in the dark for 15 minutes. After every 5 minutes a mixing protocol was applied. The ambient relative humidity was kept close to 100% in order to avoid evaporation.
5. 800 µl PBS buffer were added to the rotatable vessel (300).
6. A mixing protocol was applied.
7. A separation protocol was applied.
8. The liquid phase was removed (to waste).
9. 500 µl PBS buffer were added to the rotatable vessel (300) as cell release buffer.
10. A resuspension protocol was executed.
11. The suspended cells (930) were analyzed with a flow cytometer by directly aspirating the cell suspension from the rotatable vessel (300).

Observations:

The recovery rate for the WBCs was >85%, the scattergrams and fluorograms were identical to manual sample preparation using known protocols.

Example 6: Processing Particles with a Rotatable Vessel Having a Burst Valve Objective:

Basic operations with whole blood cell suspensions: Mixing blood with a second liquid, removing the liquid phase from the cells, and resuspending the cells in a cell resuspension buffer.

Materials:
1. A rotatable vessel (400) having a burst valve (450) made of a hydrophobic sintered porous polypropylene having a nominal pore size of 18 to 40 μm (Porex, Material XM-0294), while the other elements of the rotatable vessel (400) were made of PMMA. The rotatable vessel (400) allowed a maximal processing volume of approximately 1 ml. The peripheral waste chamber had an outer diameter of 34 mm, able to receive a total waste volume of about 6 ml.
2. Processing station (100): as in Example 1

Processing Parameters:

A program for particle (930) separation & supernatant removal:

S1: The rotatable vessel (400) was accelerated with 1000 RPM/sec to a final rotation speed of 3500 RPM, and was rotated at the constant speed of 3500 RPM for 60 sec.

S2: The rotatable vessel (400) was accelerated, from 3500 RPM to 8000 RPM, with an acceleration of 200 RPM/sec, and was rotated at a constant speed of 8000 RPM for 30 sec.

Finally, the rotatable vessel (400) was decelerated to 0 RPM with 1000 RPM/sec.

A Program for Particle Resuspension:

R1: Applying an acceleration of 25'000 RPM/sec during 1980° (=5.5 full turns) to a final speed of approximately 4000 RPM, in clockwise direction, then with a deceleration of 25'000 RMP/sec during 1980° (5.5 full turns) to a final speed of 0 RPM. This equals 3960°=a total of 11 rotations in clockwise direction.

R2: Applying an acceleration of 25'000 RPM/sec during 1980° (=5.5 full turns) to a final speed of approximately 4000 RPM, in counter-clockwise direction, then with a deceleration of 25'000 RPM/sec during 1980° (5.5 full turns) to a final speed of 0 RPM. This equals 3960°=a total 11 rotations in counter-clockwise direction.

Repeat 20 times (R1→R2).

A Program for Mixing:

M1: Applying an acceleration of 25'000 RPM/sec during 1980° (=5.5 full turns) to a final speed of approximately 4000 RPM, in clockwise direction, then with a deceleration of 25'000 RPM/sec during 1980° (5.5 full turns) to a final speed of 0 RPM. This equals 3960°=a total of 11 rotations in clockwise direction.

M2: Applying an acceleration of 25'000 RPM/sec during 1980° (=5.5 full turns) to a final speed of approximately 4000 RPM, in counter-clockwise direction, then with a deceleration of 25'000 RPM/sec during 1980° (5.5 full turns) to a final speed of 0 RPM. This equals 3960°=a total 11 rotations in counter-clockwise direction.

Repeat 5 times (M1, M2).

Experiment Conducted
1. The rotatable vessel (400) was mounted to a processing station (100).
2. 100 μl of whole blood were added into the rotatable vessel (400).
3. 900 μl PBS buffer were added.
4. A mixing protocol was executed.
5. A protocol for particle separation & supernatant removal was executed.
6. S1 60 sec at 3500 RPM
7. S2 30 sec at 8000 RPM
8. 200 μl PBS were added into the rotatable vessel (400).
9. A re-suspension protocol was executed.

Observations:

In 4: Mixing was achieved, while no liquid penetrated the burst valve (450).

In 5 and 6: While spinning at the lower speed the particles (930) were separated to the wall of the lateral collection chamber (220) under the influence of centrifugal force. During 5, no liquid was moving past the burst valve (450). When gradually accelerating to reach the higher rotation speed, the burst valve (450) was found to burst causing liquid to penetrate the burst valve (450).

In 8: A good degree of re-suspension was achieved, while no liquid was moving past the burst valve (450). The measured recovery of cells was >80%. More than 90% of the supernatant was received in the peripheral waste chamber.

Example 7: Particle Processing with a Rotatable Vessel (500) Having a Peripheral Filter (550)

Objective:

Basic operation with particle suspensions: Mixing a suspension of particles (930) with a second liquid, removing the liquid phase from the particles (930), and resuspending the particles.

Materials:
1. A rotatable vessel (500) having peripheral filter (550) was used. The maximum inner diameter of the intermediate portion was 22 mm. The peripheral filter (550) was made of a hydrophobic sintered porous polypropylene having a nominal pore size of 18 to 40 μm (Porex, Material XM-0294), while the other elements were made of PMMA. The rotatable vessel (500) allowed a maximal processing volume of approximately 1 ml. The peripheral waste chamber (560) had an outer diameter of 34 mm and was able to receive a total waste volume of about 6 ml.
2. Processing station (100): as in Example 1

Processing Parameters:

A program for particle (930) separation & supernatant removal:

S1: Accelerating with 1000 RPM/sec to a final rotation speed of 8000 RPM, maintain speed for 2 sec S2: Decelerate with 3000 RPM/sec to a final rotation speed of 5000 RPM Repeat S1→S2 during 120 sec A Program for Particle Resuspension:

R1: Applying an acceleration of 25'000 RPM/sec during 1980° (=5.5 full turns) to a final speed of approximately 4000 RPM, in clockwise direction, then with a deceleration of 25'000 RPM/sec during 1980° (5.5 full turns) to a final speed of 0 RPM. This equals 3960°=a total of 11 rotations in clockwise direction.

R2: Applying an acceleration of 25'000 RPM/sec during 1980° (=5.5 full turns) to a final speed of approx. 4000 RPM, in counter-clockwise direction, then with a deceleration of 25'000 RPM/sec during 1980° (5.5 full turns) to a final speed of 0 RPM. This equals 3960°=a total 11 rotations in counter-clockwise direction.

Repeat 20 times (R1→R2)

A Program for Mixing:

M1: Applying an acceleration of 25'000 RPM/sec during 1980° (=5.5 full turns) to a final speed of approximately 4000 RPM, in clockwise direction, then with a deceleration of 25'000 RPM/sec during 1980° (5.5 full turns) to a final speed of 0 RPM. This equals 3960°=a total of 11 rotations in clockwise direction.

M2: Applying an acceleration of 25'000 RPM/sec during 1980° (=5.5 full turns) to a final speed of approximately 4000 RPM, in counter-clockwise direction, then with a deceleration of 25'000 RMP/sec during 1980° (5.5 full turns) to a final speed of 0 RPM. This equals 3960°=a total 11 rotations in counter-clockwise direction.

Repeat 5 times (M1→M2)

Experiment Conducted:
1. The rotatable vessel (500) was mounted to a processing station (100)
2. 50 µl of a bead suspension (Fluorospheres®, with $1\times10^6$ beads/ml) were a pipetted into the rotatable vessel (500)
3. 900 µl PBS buffer were added.
4. A mixing protocol was executed.
5. A protocol for particle (930) separation & supernatant removal was executed.
6. 200 µl of PBS were added to the rotatable vessel (500).
7. A resuspension protocol was executed.

Observations:
In 4.: Mixing was achieved, while no liquid moved past the peripheral filter (550).
In 5.: The supernatant crossed the peripheral filter (550) while the particles remained in the lateral collection chamber (220).
In 7.: The particles (930) were well suspended while no liquid crossed the peripheral filter (550). The recovery of particles was >90%. More than 90% of the supernatant was received in the peripheral waste chamber (560).

Example 8: Isolation of Nucleic Acid from a Sample Matrix Using Silica Beads (930) and Chaotropic Agents In order to isolate and analyze nucleic acids (NA), such as DNA and RNA from a biological source, such as from serum, blood, plasma, homogenized tissue, culture liquids, the NAs of interest often needs to be isolated and purified from disturbing matter in the sample potentially causing inhibition of analytic reactions. The NAs may, for example, be genomic DNA or mRNA from a patient, viral DNA or RNA found in a sample, or the like.

The aim of the current Example was to extract the nucleic acids from WBCs for downstream PCR (for example, in order to determine the viral load in WBC).

Reagents Used:
Bead Suspension:

| 10.00 g | Silica particles (930) (diameter range 1 to 10 µm) |
| 1.000 l | suspended in abs. ethanol resulting in 1l of bead suspension |

Lysis Buffer:

| 5.50 M | Guanidinium-thiocyanate |
| 0.04 M | TRIS pH 7.5 |
| 9.00 g | Triton X100 |
| 0.02 M | 1,4-Dimercapto-2,3-butandiol (DTT) |
| 10 mg | polyA (GE Healthcare) |
| 1.000 l | completed with water to 1l lysis buffer |

Wash Buffer:

| 0.66 mM | TRIS pH 7.5 |
| 0.16 g | Triton X100 |
| 10 mg | polyA (GE Healthcare) |
| 185 g | Water |
| 650 g | Ethanol 96% |
| ~1.0 l | water added to result in 1l wash buffer |

Elution Buffer:

| 50 mg | Dodecyl-maltoside |
| 3.30 mM | Tris pH 7.5 |
| 5 mg | polyA (GE Healthcare) |
| 1.000 L | complete with water to 1l elution buffer |

Materials:
1. A rotatable vessel (300) according to FIG. 3B with a lateral collection chamber (220) of 500 µm width and 250 µm depth was used. The maximum inner diameter of the intermediate portion (206) was 28 mm. The volume within the vertical grooves (302) was about 100 µl. The volumes of the lateral collection chamber (220) and the inner space (202) of the lower portion (207) were each approximately 1.2 ml, creating a maximum processing volume of about 1 ml. The rotatable vessel (300) was made of polypropylene, assembled from a transparent lower part and an opaque upper part which were both produced by injection molding and then laser-sealed to form a tight rotatable vessel (300).
2. Processing station (100): as in Example 1

Processing Parameters:
M1: Mixing protocol: as in Example 1
S1: Separation protocol: as in Example 2
R1: Resuspension protocol: as in Example 3

Experiment Conducted:
Cell Lysis & NA-Binding to Silica Beads (930):
1. Obtain about $5\times10^5$ WBCs as described previously from 100 µl of whole blood.
2. Add 150 µl deionized water to the WBCs. Perform M1.
3. Add 350 µl of lysis buffer. Perform M1.
4. Incubate 2 min at 25° C.
5. Add 100 µl of bead suspension. Perform M1.
6. Incubate 10 min at 25° C., resuspend beads (930) every 60 sec, with M1.

Washing:
7. Run separation protocol, with S1.
8. Remove supernatant and discharge it to waste.
9. Add 500 µl wash buffer.
10. Resuspend beads (930) in wash buffer, with R1.
11. Run separation protocol, with S1.
12. Remove supernatant and discharge it to waste.
13. Repeat steps 9 through 11 two more times Elution:
1. Add 250 µl elution buffer, having a temperature of 80° C.
2. Perform a resuspension and mix step, R1 then M1.
3. Perform a separation step, with S1.
4. Remove supernatant for further processing.

Observation:
The final liquid collected from the rotatable vessel (300) contained the isolated and purified NAs ready for further analysis such as by PCR, while the beads (930) remained within the rotatable vessel (300).

Example 9: Enrichment of Rare Cells (930) from a Liquid

Objective:

In order to analyze rare cells (930) in a liquid biological sample (920) it is often required to concentrate the rare cells (930) of interest. This often requires large and bulky containers using up a considerable amount of space within an automated system (1). The rotatable vessel (300) described herein can be used to concentrate rare cells (930), as follows:

Materials:
1. Rotatable vessel (300) as in Example 8
2. Processing station (100) as in Example 8

Experiment Conducted:

Separation and Resuspension Protocols as in Example 8
1. Procedure starts with 5 ml cell suspension containing the rare cells (930).
2. Add 1 ml of cell suspension into the rotatable vessel (300).
3. Perform a separation protocol.
4. Remove cell-free supernatant from the rotatable vessel (300).
5. Repeat 4× steps 2 to 4.
6. Add 250 µl of PBS-buffer.
7. Perform a resuspension protocol.
8. Retrieve pre-concentrated cell suspension from the rotatable vessel (300) for further processing or analysis.

Observation:

The cells (930) could be concentrated by more than 10 fold.

Example 10

In a first step, a sample including a large amount of cells from a patient is analyzed with regard to statistical data. For instance, 50'000 cells are measured in four fluorescence channels, providing four integral fluorescence values per cell. Additionally, a cellular diameter is measured using a suitable marker. Further, an integral cell scatter value is measured using a reflection mode. The geometrical resolution in x/y is 15×3 µm, wherein each cell is attributed specific coordinates.

The collected data are, in a second step, processed using predefined criteria, determining the relative presence of, for example, six classes of cells. For each class of cells, the relative concentration is calculated.

In a third step, a high (3×2 µm) resolution image is acquired for each of the six classes of cells. A limited number of cells such as 10 representative cells is analyzed in all or a limited number of fluorescence channels, using the coordinates obtained in the first step.

As a fourth step, the data from all preceding steps are presented and reported to the user. In particular, from each cell class a limited number of cells is reported along with an absolute or relative occurrence of the respective class. Further, the expression level of a marker may be reported.

Example 11

The first and the second steps are as in Example 10.

In a third step, from cells having an unusual (expression) pattern or from cells having an expression pattern related to a sickness, a limited number of cells is imaged at a higher resolution, optionally by used of a fifth wavelength, in order to provide morphological data on those unexpected cells or cells related to a sickness.

Example 12

A first step is employed to conduct a high resolution scan of a low and limited number of cells (for instance, about 200 cells) to obtain morphological data.

A second step is used to analyze the morphological data (by a user or by an automated system) and identify cells or classes of cells of interest.

A third step serves to analyze the sample at a high throughput and a low resolution.

In this example either a scanner is used supporting at least two resolutions. The switch of resolution can be done by altering data acquisition frequency, rotational speed, stepsize of the scanner or by altering a slit or aperture. The lower resolution mode is used to measure the data for statistical purposes, while the higher resolution mode is used to obtain the morphological data.

Alternatively, two measuring means may be used, one measuring means measuring at a lower resolution (at higher speed) and one measuring means measuring at a higher resolution (at lower speed), wherein the first measuring means acquires the data used for the statistical data, and wherein the second measuring means acquires the data used for the morphological data. The first and second means may be based on laser-scanning, or only the first measuring means may be laser-scanning based while the second measuring means is camera-based. Any other combination of appropriate measuring means may be used as known to the skilled person.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for separating particles from a liquid biological sample and re-suspending the particles in a secondary liquid, the method comprising:
   a) introducing the liquid biological sample comprising the particles into a rotatable vessel through a top opening of the rotatable vessel such that the liquid is held by a lower portion of the rotatable vessel, wherein the rotatable vessel comprises
      a longitudinal axis about which the vessel is rotatable,
      an upper portion comprising the top opening for receiving the liquid comprising the particles, the lower portion for holding the liquid while the rotatable vessel is resting, the lower portion comprising a bottom, and an intermediate portion located between the upper portion and the lower portion, the intermediate portion comprising a lateral collection chamber for holding the liquid while the rotatable vessel is rotating;

b) rotating the rotatable vessel about its longitudinal axis at a rotational speed, wherein the liquid comprising the particles is moved to the lateral collection chamber by centrifugal force, and wherein the centrifugal force is sufficient to sediment the particles in a region of sedimentation of an inner wall of the lateral collection chamber;

c) decelerating at a rate of from 50 rpm/s to 1000 rpm/s and ultimately stopping the rotation of the rotatable vessel, wherein the liquid flows back to the lower portion of the rotatable vessel, wherein an angular deceleration is not sufficient to detach the particles from the inner wall of the lateral collection chamber by causing shearing forces between wall and liquid such that at least a part of the particles remain attached to the inner wall of the lateral collection chamber, thereby separating at least the part of the particles from the liquid;

d) withdrawing the liquid from the bottom of the rotatable vessel while leaving the particles in the lateral collection chamber;

e) adding the secondary liquid to the rotatable vessel through its top opening;

f) rotating the rotatable vessel about its longitudinal axis in a first direction; and g) decelerating and ultimately stopping the rotation of the rotatable vessel, wherein an angular acceleration in step f) and/or an angular deceleration in step g) is sufficient to detach at least a part of the particles from the inner wall of the lateral collection chamber by causing shearing forces between wall and liquid, thereby re-suspending the particles in the secondary liquid and wherein the angular acceleration in step f) has a rate of at least 500 rpm/s while the angular deceleration in step g) has a rate of at least 500 rpm/s.

2. The method according to claim 1, wherein steps f) and g) are repeated one or more times.

3. The method according to claim 1, further comprising after step g), h) rotating the rotatable vessel about its longitudinal axis in a second direction opposite to the first direction at a rotational speed; and i) decelerating and ultimately stopping the rotation of the rotatable vessel, wherein an angular acceleration in step h) and/or an angular deceleration in step i) is sufficient to detach at least a part of the particles from the inner wall of the lateral collection chamber by causing shearing forces between wall and liquid and wherein the angular acceleration in step h) has a rate of at least 500 rpm/s while the angular deceleration in step i) has a rate of at least 500 rpms/s.

4. The method according to claim 3, wherein steps f) and g), steps h) and i), and/or steps f) through i) are repeated one or more times.

5. The method according to claim 1, wherein the rate of deceleration in step c) is smaller than any of the rates of acceleration or deceleration in steps f) or g).

6. The method according to claim 1, wherein the rate of deceleration in step c) is from 50 rpm/s to 400 rpm/s.

* * * * *